(12) United States Patent
Laug

(10) Patent No.: US 6,521,593 B1
(45) Date of Patent: Feb. 18, 2003

(54) METHODS FOR INHIBITING BRAIN TUMOR GROWTH

(75) Inventor: Walter E. Laug, La Crescenta, CA (US)

(73) Assignee: Childrens Hospital Los Angeles, Los Angeles, CA (US)

(*) Notice: Subject to any disclaimer, the term of this patent is extended or adjusted under 35 U.S.C. 154(b) by 0 days.

(21) Appl. No.: 09/489,391

(22) Filed: Jan. 21, 2000

Related U.S. Application Data

(60) Provisional application No. 60/118,126, filed on Feb. 1, 1999.

(51) Int. Cl.[7] ............................................... A61K 38/12

(52) U.S. Cl. .......................................... 514/9; 530/317

(58) Field of Search ................... 514/2, 12, 9; 530/300, 530/317, 330

(56) References Cited

PUBLICATIONS

Wermuth et al , J. Am. Chem. Soc. 119:1328–1335, 1997.*
Rudinger, Peptide Hormones, University Park Press, pp. 1–7, 1976.*
Clark et al., American Journal of Pathology 148:1407–1421, 1996.*
Gladson et al., Journal of Cell Science 108:947–956, 1995.*
Chistofidou–Solomidou et al., American Journal of Pathology 151:975–983, 1997.*

* cited by examiner

*Primary Examiner*—Sheela Huff
*Assistant Examiner*—Larry R. Helms
(74) *Attorney, Agent, or Firm*—Olson & Hierl, Ltd.

(57) ABSTRACT

The present invention describes methods for inhibition of tumor growth in the brain, using antagonists of integrins such as $\alpha_v\beta_3$ and $\alpha_v\beta_5$. Antagonists of the present invention can inhibit angiogenesis in brain tumor tissue. They can also inhibit vitronectin and tenascin-mediated cell adhesion and migration in brain tumor cells. They can further induce direct brain tumor cell death.

4 Claims, 14 Drawing Sheets

METHODS FOR INHIBITING BRAIN TUMOR GROWTH

RELATED APPLICATION

This application claims the benefit of a provisional application Ser. No. 60/118,126, filed on Feb. 1, 1999 which is hereby incorporated by reference.

BACKGROUND OF THE INVENTION

1. Area of the Art

The invention relates generally to inhibition of tumor growth and specifically to inhibition of brain tumor growth.

2. Description of the Prior Art

Throughout this application various references are referred to within parentheses. Disclosures of these publications in their entireties are hereby incorporated by reference into this application to more fully describe the state of the art to which this invention pertains. Full bibliographic citation for these references may be found at the end of this application, preceding the claims.

Brain tumors, like other solid tumors, require a perpetually increasing blood supply to maintain continuous growth beyond 1–2 mm$^3$ (1,2). This is accomplished through angiogenosis, a process which occurs in response to endothelial growth factors released by tumor cells. Angiogenesis involves the induction of endothelial cell proliferation from quiescent microvasculature, migration of neoendothelium toward the tumor bed and, finally, maturation into a new capillary network (3). Brain tumors are the most angiogenic of all human neoplasias. The principal angiogenic factors demonstrated by either in situ hybridization or specific antibodies in tissue sections of patients with glioblastoma and medulloblastoma, the most common malignant brain tumors, are vascular endothelial growth factor (VEGF) and basic fibroblast growth factor (bFGF) (4–7). In fact, VEGF expression and microvessel density in glial tumors directly correlate with the degree of malignant characteristics and overall outcome (8–9).

Recent evidence suggests that angiogenesis is regulated by the activation of endothelial cell integrins, a family of transmembrane receptors which direct cell adhesion to extracellular matrix (ECM) proteins by binding to the amino acid sequence Arg-Gly-Asp (RGD)(10). In response to bFGF and VEGF, endothelial cells upregulate the expression of integrins $\alpha_v\beta_3$ and $\alpha_v\beta_5$, respectively (11–13). Glioblastomas and their associated vascular endothelium have been found to express the integrins $\alpha_v\beta_3$ and $\alpha_v\beta_5$ (14,15). Integrin-mediated adhesion results in the propagation of intracellular signals which promote cell survival, proliferation, motility and capillary sprouting (16,17). Failure of these integrins to bind ligand results in endothelial cell apoptosis (18,19). The matrix glycoprotein, vitronectin, serves as ligand for $\alpha_v\beta_3$ and $\alpha_v\beta_5$ and is produced at the leading invasive edge by malignant gliomas (15,20). Together, these findings suggest a complex paracrine interaction between tumor cells, brain ECM and endothelial cell integrins for the continued angiogenesis and growth of malignant brain tumors.

Studies using the anti-$\alpha_v\beta_3$ antibody, LM-609, or an RGD cyclic peptide antagonist of $\alpha_v\beta_3$ and $\alpha_v\beta_5$ which prevents integrin-ECM interactions, have demonstrated an anti-angiogenesis response in the chicken chorioallantoic membrane (CAM) and a mouse chimera model (21–23). Other agents which act upon alternative sites of the angiogenesis pathway, such as antibodies to VEGF or its tyrosine kinase receptor flt, have also been effective in inhibiting angiogenesis (24,25).

Prior studies have shown that the attachment of breast carcinoma, melanoma and HT29-D4 colonic adenocarcinoma cells to vitronectin is dependent on $\alpha_v$, $\alpha_v\beta_3$ and $\alpha_v\beta_5$, respectively (51–53). Vitronectin, which is produced by tumor and endothelial cells, is recognized by $\alpha_v\beta_3$ and $\alpha_v\beta_5$ and is an ECM protein found at sites of tumor invasion and neovascularization (54–55). Thus, in addition to supporting endothelial cell survival through $\alpha_v$, ligation, and hence angiogenesis, vitronectin expression may further enhance the adhesion of tumor and endothelial cells which express $\alpha_v\beta_3$ and $\alpha_v\beta_5$ integrins, thereby promoting their invasion. In one study using a SCID mouse/human chimeric model for breast cancer, tumor invasion was considerably reduced following the administration of the anti-$\alpha_v\beta_3$ antibody LM-609, suggesting a direct effect upon the tumor cell biology through a $\alpha_v\beta_3$ blockade (56).

Brain tumors, because of their highly invasive nature and degree of angiogenesis, afford an excellent model with which to further study the importance of integrins in tumor progression. Multiple studies have shown that microvessel density correlates with outcome and malignant grade in astrocytomas (57–59). Angiogenesis inhibitors, such as TNP-470, thrombospondinl and platelet factor 4, have been introduced into experimental brain tumors and have shown an inhibition of tumor growth (60–62). However, to date, no study has examined the effect of integrin antagonism on brain tumor invasion and angiogenesis. Therefore, a need exists to study the effect and thus provide a novel method for treating brain tumors.

SUMMARY OF THE INVENTION

The present invention is based on the surprise discovery that targeted antagonism of integrins, specifically $\alpha_v\beta_3$ and $\alpha_v\beta_5$, can substantially inhibit brain tumorigenesis in vivo. It is also based on the discovery that the microenvironment of the brain tumor is critical to the tumor behavior and in determining its responsiveness to such biologically directed therapies. The invention is further based on the discovery that integrin antagonism can have an anti-tumorigenic effect independent of anti-antiogenesis, which may act synergistically to retard tumor growth. For example, it is a discovery of the present invention that integrin antagonism may induce direct brain tumor cell death.

Accordingly, one aspect of the present invention provides a method of inhibiting tumor growth in the brain of a host. The method comprises administering to the host in need of such an inhibition a therapeutically effective amount of an antagonist of an integrin.

In one embodiment of the present invention, the integrin may be $\alpha_v\beta_3$ or $\alpha_v\beta_3$. The antagonist may be a polypeptide antagonist of $\alpha_v$, an antibody against $\alpha_v\beta_3$, an antibody against $\alpha_v\beta_5$ or a combination of antibodies respectively against $\alpha_v\beta_3$ and $\alpha_v\beta_5$.

Another aspect of the present invention provides a method for inhibiting angiogenesis in a tumor tissue located in the brain of a host. The method comprises administering to the host a composition comprising an angiogenesis-inhibiting amount of an antagonist of an $\alpha_v$ integrin.

In one embodiment of the present invention, the intergrin is $\alpha_v\beta_3$ or $\alpha_v\beta_5$. The antagonist is a polypeptide antagonist of $\alpha_v$, an antibody against $\alpha_v\beta_3$, an antibody against $\alpha_v\beta_5$ or a combination of antibodies respectively against $\alpha_v\beta_3$ and $\alpha_v\beta_5$.

A further aspect of the present invention provides a method of inhibiting ECM-dependent cell adhesion of brain tumor cells growing in the brain of a host. The method comprises administering to the host a therapeutic effective amount of an antagonist of an ax integrin, i.e., integrins $\alpha_v\beta_3$ or $\alpha_v\beta_5$. In one embodiment of the present invention, the antagonist is a polypeptide antagonist of $\alpha_v$ or a combination of antibodies respectively against $\alpha_v\beta_3$ and $\alpha_v\beta_5$.

Yet another aspect of the present invention provides a method of inhibiting vitronectin-dependent cell migration in brain tumor cells growing in the brain of a host. The method comprises administering to the host a therapeutically effective amount of an antagonist to as In one embodiment of the present invention, the antagonist is a polypeptide antagonist of $\alpha_v$ or an antibody against $\alpha_v\beta_3$.

A further aspect of the present invention provides a method of inducing apoptosis in tumor cells growing in the brain of a host. The method comprises administering to the host a therapeutically effective amount of an antagonist of an integrin.

In one embodiment of the present invention, the integrin may be $\alpha_v\beta_3$ or $\alpha_v\beta_5$. The antagonist may be a polypeptide antagonist of $\alpha_v$.

The methods of the present invention are well suited for use in treating brain tumors in vivo. The present invention provides a novel therapeutic approach to treat brain tumors.

DESCRIPTION OF THE FIGURES

The above-mentioned and other features of this invention and the manner of obtaining them will become more apparent, and will be best understood, by reference to the following description, taken in conjunction with the accompanying drawings. These drawings depict only a typical embodiment of the invention and do not therefore limit its scope. They serve to add specificity and detail, in which.

DETAILED DESCRIPTION OF THE INVENTION

Figure 1A:
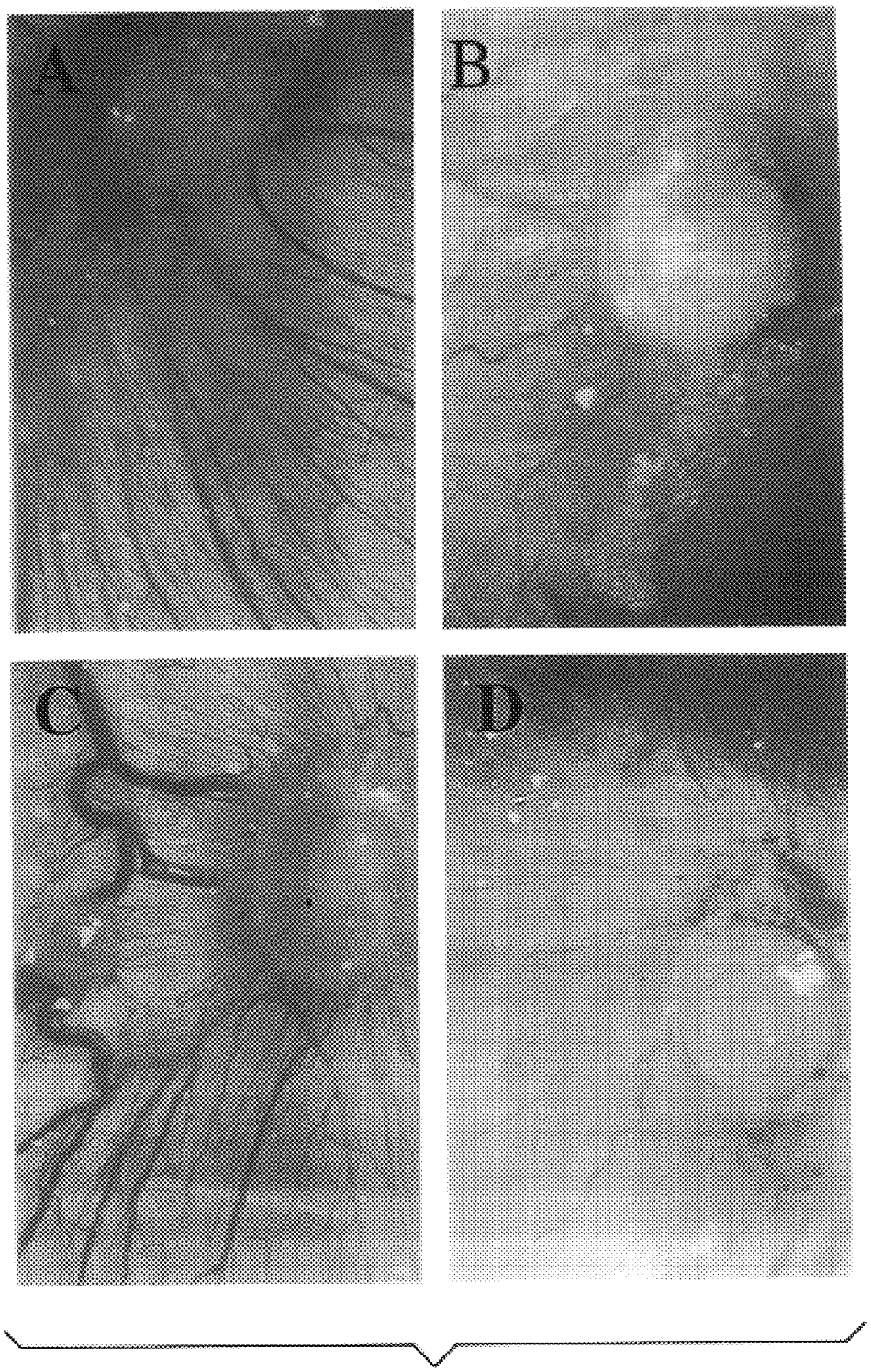
FIGS. 1(A–D) show the inhibition of angiogenesis (a) and tumor growth on the CAM (b) by $\alpha_v$-antagonist.

One aspect of the present invention provides a method of inhibiting tumor growth in the brain of a host, comprising administering to the host in need of such an inhibition a therapeutically effective amount of an antagonist of an integrin.

The method of the present invention may be used to treat any tumors that grow in the brain, as long as the growth of tumors in the brain requires the interaction of the integrin with its ligand. Examples of such a tumor include, but are not limited to, glioblastoma, medulloblastoma (astrocytoma, other primitive neuroectoderma and brain stem glioma cancers). For the purpose of the present invention, preferably, the tumor growth is located intracerebrally in the brain of a host. The host may be any mammal, including, but not limited to, rat and human. The tumor growth is inhibited if the growth is impaired by the treatment.

For the purpose of the present invention, an integrin is any member of a specific family of homologous heterodimeric transmembrane receptors. The receptors direct cell adhesion by binding to the amino acid sequence Arg-Gly-Asp (RGD). The receptors may be expressed on both tumor and normal cells. The characteristic of integrins are well known and well characterized in the art and are described in detail in the cited references (1, 2), the relevant content of which is incorporated herein by reference. Examples of integrins include, but are not limited to, the ax family, such as $\alpha_v\beta_3$, $\alpha_v\beta_5$, $\alpha_v\beta_1$, $\alpha_v\beta_6\alpha_v\beta_8$ and the like.

An antagonist of an integrin is a molecule that blocks or inhibits the physiologic or pharmacologic activity of the integrin by inhibiting the binding activity of the integrin, a receptor, to its ligand, various matrix proteins, including, but not limited to, vitronectin, tenascin, fibronectin and collagen I. In one embodiment of the present invention, an antagonist of an integrin may be an antagonist of integrin $\alpha_v\beta_3$ or integrin $\alpha_v\beta_3$. Preferred integrin antagonists can be either a monoclonal antibody, a fragment of the monoclonal antibody, or a peptide.

For example, an antagonist of $\alpha_v\beta_3$ may be any factor that inhibits the binding of $\alpha_v\beta_3$ to one of its multiple ligands, namely vitronectin or tenascin. Examples of antagonists of $\alpha_v\beta_3$ are described in the PCT publications WO 96/37492 and WO 97/45137, the relevant content of which is incorporated herein by reference.

Likewise, an antagonist of $\alpha_v\beta_5$ may be any factor that inhibits the binding of $\alpha_v\beta_5$ to its ligand, namely vitronectin. Examples of antagonists of aver are described in the PCT publication WO 97/06791, the relevant content of which is incorporated herein by reference.

In one embodiment of the present invention, the antagonist is a polypeptide antagonist of $\alpha_v$, namely, a polypeptide antagonist of $\alpha_v\beta_3$ and $\alpha_v\beta_5$. Preferably, the polypeptide is an Arg-Gly-Asp (RGD)-containing polypeptide. In one embodiment, the polypeptide antagonist is an RGD cyclic pentapeptide antagonist of $\alpha_v$.

In accordance with another embodiment of the present invention, the antagonist may be a monoclonal antibody immunospecific for $\alpha_v\beta_3$ or $\alpha_v\beta_5$. Alternatively, it may be a combination of antibodies respectively against $\alpha_v\beta_3$ and $\alpha_v\beta_5$. In one embodiment, a monoclonal antibody immunospecific for $\alpha_v\beta_3$ has the immunoreaction characteristics of a monoclonal antibody designated LM-609. In another embodiment of the present invention, a monoclonal antibody immunospecific for $\alpha_v\beta_5$ has the immunoreaction characteristics of a monoclonal antibody designated P1-F6. Both the LM-609 antibody and P1-F6 antibody are well known in the industry and are commercially available through Chemicon, Temecula, Calif.

For the purpose of the present invention, the antagonists may be used alone or in combination with each other in a method of the present invention for inhibiting tumor growth in the brain.

The therapeutically effective amount is an amount of antagonist sufficient to produce a measurable inhibition of a tumor growth in the brain of a host being treated. Inhibition of tumor growth can be determined by microscopic measurement after staining, as described herein, by mouse brain MRI scanning, or by 3H-Thymidin Incorporation, which methods are well known to one skilled in the art.

Insofar as an integrin antagonist can take the form of an RGD-containing peptide, an anti-$\alpha_v\beta_3$ monoclonal antibody or fragment thereof, an anti-$\alpha_v\beta_5$ monoclonal antibody or a fragment thereof, or a combination of the monoclonal antibodies of $\alpha_v\beta_3$ and $\alpha_v\beta5$, it is to be appreciated that the potency, and therefore the expression, of a "therapeutically effective amount" can vary. However, as shown by the present assay methods, one skilled in the art can readily assess the potency of a candidate antagonist of this invention.

The potency of an antagonist can be measured by a variety of means including, but not limited to, inhibition of angiogenesis in the CAM assay, in the in vivo brain tumor assay, and by measuring inhibition of the binding of natural ligands to integrins such as $\alpha_v\beta_3$ or $\alpha_v\beta_5$, all as described herein, and like assays.

The dosage ranges for the administration of the antagonist depend upon the form of the antagonist and its potency to a particular integrin. One skilled in the art can find out the proper dosage for a particular antagonist in view of the disclosure of the present invention without undue experimentation. The dosage should be large enough to produce the desired effect in which tumor growth in the brain is inhibited. The dosage should not be so large as to cause adverse side effects, such as brain edema or the rapid release of cytokines from brain tumors inducing kachexia, for example, when an integrin antagonist of the present invention is administered in the form of a polypeptide. The dosage per kg body weight can vary from 1 to 20 mg, in one or more dose administrations daily, for one or several days or indefinitely. When an integrin antagonist of the present invention is administered in the form of a monoclonal antibody, the dosage can vary from 1 to 20 mg/kg, in one dose administrations once to twice weekly for an indefinite time.

The polypeptide or monoclonal antibodies of the present invention can be administered parenterally by injection or by gradual infusion over time. Although the tissue to be treated is most often by intraperitoneal or subcutaneous (antibody) administration, the antagonists of the present invention may also be administered intraocularly, intravenously, intramuscularly, intracavity, transdermally, and can be delivered by peristaltic means.

The compositions are administered in a manner compatible with the dosage formulation and in a therapeutically effective amount. The quantity to be administered and timing of administration depend on the subject to be treated, capacity of the subject's system to utilize the active ingredient, and degree of therapeutic effect desired. Precise amounts of the active ingredient required to be administered depend on the judgement of the practitioner and are peculiar to each individual. However, suitable dosage ranges for systemic application are disclosed herein and depend on the route of administration. Suitable regimes for administration are also variable but are typified by an initial administration, followed by repeated doses at one or more hour intervals by a subsequent injection or other administration.

In accordance with one embodiment of the present invention, the present invention also provides a pharmaceutical composition useful for practicing the therapeutic methods described herein. The compositions contain an antagonist of the present invention in combination with a pharmaceutically acceptable carrier. As used herein, the terms "pharmaceutically acceptable," "physiologically tolerable" and grammatical variations thereof, as they refer to compositions, carriers, diluents and reagents, are used interchangeably and represent that the materials are capable of administration to or upon a mammal without the production of undesirable physiological effects.

Preparations for parental administration of a peptide or an antibody of the invention include sterile aqueous or non-aqueous solutions, suspension, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parental vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present, such as, for example, antimicrobials, antioxidants, chelating agents, and inert gases and the like.

Another aspect of the present invention provides a method for inhibiting angiogenesis in a tumor tissue located in the brain of a host. The method comprises administering to the host a composition comprising an angiogenesis-inhibiting amount of an antagonist of an integrin.

As discussed in the background section, angiogenesis is the formation of a neovascular network from pre-existing host vessels and is required for tumor growth beyond 1–2 mm$^3$. For the purpose of the present invention, angiogenesis is inhibited if angiogenesis and the disease symptoms mediated by angiogenesis are ameliorated.

In one embodiment of the present invention, the tumor tissue is located intracerebrally in the brain of a host. The host may be any mammal. Examples of the host include, but are not limited to, mouse, rat and human.

The dosage ranges for the administration of the antagonist depend upon the form of the antagonist and its potency to a particular integrin. One skilled in the art can find out the proper dosage for a particular antagonist in view of the disclosure of the present invention without undue experimentation. The dosage should be large enough to produce the desired effect in which angiogenesis and the disease symptoms mediated by angiogenesis are ameliorated. The dosage should not be so large as to cause adverse side effects, such as brain edema due to rapid tumor lysis with cytokine release or hemorrhage.

In one embodiment of the present invention, an antagonist of an integrin may be an antagonist of integrin $\alpha_v\beta_3$ or integrin $\alpha_v\beta_5$. Preferred integrin antagonists can be either a monoclonal antibody or a peptide. In one embodiment of the present invention, the antagonist is a polypeptide antagonist of $\alpha_v$, namely, a polypeptide antagonist of $\alpha_v\beta_3$ and $\alpha_v\beta_5$. Preferably, the polypeptide is an Arg-Gly-Asp (RGD)- contained polypeptide. In one embodiment, the polypeptide antagonist is an RGD cyclic pentapeptide antogonist of $\alpha_v$.

In accordance with another embodiment of the present invention, the antagonist may be an antibody against $\alpha_v\beta_3$ and a combination of antibodies respectively against $\alpha_v\beta_3$ and $\alpha_v\beta_5$.

The therapeutically effective amount is an amount of antagonist sufficient to produce a measurable inhibition of angiogenesis in the tisuue being treated, i.e., an angiogenesis-inhibiting amount. Inhibition of angiogenesis can be measured in situ by immunohistochemistry, as described herein, or by other methods known to one skilled in the art.

In accordance with one embodiment of the present invention, the present invention also provides a pharmaceutical composition useful for practicing the therapeutic methods described herein. The compositions contain an antagonist of the present invention in combination with a pharmaceutically acceptable carrier.

A further aspect of the present invention provides a method of inhibiting ECM-dependent cell adhesion in brain tumor cells growing in the brain of a host, comprising administering to the host a therapeutically effective amount of an antagonist to integrins $\alpha_v\beta_3$ and $\alpha_v\beta_5$.

For the purpose of the present invention, ECM-dependent cell adhesion includes any cell adhesion that is ECM-depedent and that is mediated by $\alpha_v$-integrins. Examples of such adhesion include, but are not limited to, vitronectin-dependent cell adhesion and tenascin-dependent cell adhesion. It is a discovery of the present invention that human brain tumors may produce vitronectin and tenascin, and those ECM play an important role in tumor cell adhesion and migration by interacting with integrins. For the purpose of the present invention, the inhibition is achieved if tumor cell adhesion to ECM is reduced.

The phrase "therapeutically effective amount" as used herein indicates an amount of antagonist that is sufficient so that ECM-mediated tumor cell adhsion is reduced. Cell adhesion can be measured by the methods described herein and by the methods commonly known in the art.

In accordance with one embodiment of the present invention, the antagonist may be a polypeptide antagonist of $\alpha_v$ or a combination of antibodies respectively against $\alpha_v\beta_3$ and $\alpha_v\beta_5$. For example, the antagonist may be an RGD cyclic pentapeptide antagonist of $\alpha_v$ or a combination of monoclonal antibodies designated LM-609 and P1-F6.

Another aspect of the present invention provides a method of inhibiting vitronectin-dependent cell migration in brain tumor cells growing in the brain of a host, comprising administering to the host a therapeutically effective amount of an antagonist to $\alpha_v\beta_3$.

For the purpose of the present invention, the inhibition is achieved if tumor cell migration is reduced.

The phrase "therapeutically effective amount" as used herein indicates an amount of antagonist that is sufficient so that vitronectin-mediated tumor cell migration is reduced. Cell migration can be measured by the methods described herein and by the methods commonly known in the art.

In accordance with one embodiment of the present invention, the antagonist may be a polypeptide antagonist of $\alpha_v$ or a monoclonal antibody immunoreactive against $\alpha_v\beta_3$. For example, the antagonist may be an RGD cyclic pentapeptide antagonist of $\alpha_v$ or a monoclonal antibody designated LM-609.

The present invention also provides a method of inducing apoptosis in tumor cells growing in the brain of a host. The method comprises administering to the host a therapeutically effective amount of an antagonist of an integrin.

For the purpose of the present invention, brain tumor cell apoptosis is induced if an increased amount of tumor cell apoptosis is observed in brain after the administration of the antagonist. The therapeutically effective amount is an amount of antagonist sufficient to produce a measurable tumor cell apoptosis in the brain of a host being treated. Tumor cell apoptosis in brain may be measured by methods described herein or commonly known in the art.

In accordance with one embodiment of the present invention, the integrin may be $\alpha_v$, $\alpha_v\alpha_v\beta_3$ or $\alpha_v\beta_5$. The antagonist may be a polypeptide antagonist of $\alpha_v$.

EXAMPLES

Materials and Methods

Materials: The active cyclic RGD pentapeptide EMD 121974, cyclo(Arg-Gly-Asp-D-Phe-[N-Me]-Val), and the inactive control peptide cRAD (EMD 135981) were provided by A. Jonczyk, Ph.D., Merck KgaA, Darmstadt, Germany. The monoclonal antibodies LM609 and P1F6 have been described (13). The brain tumor cell lines DAOY and U87MG were purchased from ATCC, Rockville, Md. Primary cultures of human brain capillary endothelial cells were provided by M. Stins, Ph.D., Childrens Hospital, Los Angeles (49). Human vitronectin was purchased from Promega, Madison, Wis.

FACS analysis: A FACScan cytometer (Becton-Dickinson, San Jose) was used. Conditions were as previously described (43). Primary antibodies were LM 609 and P1 F6 at 11:100, and secondary Ab was FITC labeled goat anti-mouse IgG at 1:250. Apoptosis determination was as per the manufacturer's instruction (Clontech, Palo Alto, Calif., Apo Alert Annexin V-FITC Apoptosis kit).

Adhesion: Assay conditions were as previously described (15). Non-tissue culture treated wells incubated overnight at 4° C. with vitronectin (1–10 µg/ml PBS), washed and blocked for 30 min. with heat denatured 1% BSA in PBS, followed by washing with PBS. Control and test cells, pre-incubated at 37° C. with the test substance (20 µg/ml) in adhesion buffer for 30 min. were plated into wells ($5\times10^4$ cells/well) and incubated for 1 hr at 37° C. After gentle washing of the wells with adhesion buffer, adhering cells were fixed and stained with crystal violet, the dye solubilized in methanol and the OD determined at 600° A.

Migration: Transwell polycarbonate filters (8 µm pore size) were incubated for 30 min. at 37° C. with vitronectin in PBS (1 µg/ml on the upper side and 10 µg on the bottom side), blocked for 30 min. with 1% heat denatured BSA and washed with PBS. Test cells ($5\times10^5$/well) were added in adhesion buffer containing the test substances indicated (20 µg/ml) and incubated for 4 hrs at 37° C. with the lower chamber containing adhesion buffer. Cells in the upper chamber were removed with a cotton swab and cells on the bottom part of the filter were fixed and stained with crystal violet and the number of migrated cells determined by counting.

Apoptosis: Adhesion conditions were as above, except that 12 well plates covered with vitronectin and $5\times10^5$ cells/well were plated in adhesion buffer. After 30 min. of incubation at 37° C., the adhesion buffer was replaced with buffer containing 20 µg/ml of active cRGD or inactive cRAD peptide and incubated further for 4 hrs. Attached cells were trypsinized and combined with the detached cells in the supernatant and then examined for the presence of apoptotic cells using the Apo Alert Annexin V-FITC apoptosis kit (Clontech).

CAM assay: Egg supplier and preparation have been described earlier (23). Tumor cells were plated in 50 μl PBS at 4×10⁶ cells/egg for DAOY and 3.5×10⁶ cells/egg for U87MG. Cells were grown to tumors for 7 days, then harvested under sterile conditions, trimmed to similar sizes and repeated onto the CAM of 10-day-old embryos. The following day the active or inactive peptide (100 μg/egg) was injected into a CAM vein. Tumors were photographed in situ after 7 days of growth, then harvested, weighed and fixed in 4% buffered formalin and embedded in paraffin. After serial sectioning, slides were stained with hematoxilin and eosin.

Brain tumor model: Details of the model have been described by us (31). Tumor cells (10⁶/10 μl PBS) were injected intracerebrally at the coordinates mentioned. Intraperitoneal treatment with the active cRGD or the inactive cRAD peptide (100 μg/50 μl/mouse) was initiated on day 3 after implantation for U87MG and on day 10 for DAOY cells and repeated daily until cachexia and/or moribund status occurred. The animals were then sacrificed by $CO_2$ anesthesia, the brains removed and either snap frozen in liquid nitrogen or fixed in buffered formalin, embedded in paraffin and the cut sections stained with Hematoxylin-Eosin.

Subcutaneous tumor growth: For subcutaneous tumor growth, the cells (10⁶ mouse) were injected s.c. below the right shoulder pad immediately following intracerebral injection.

Animal studies: Animal studies were done according to the NIH guidelines and approved by the local animal care committee.

Experiments

Angiogenesis on CAM

Figure 1B:
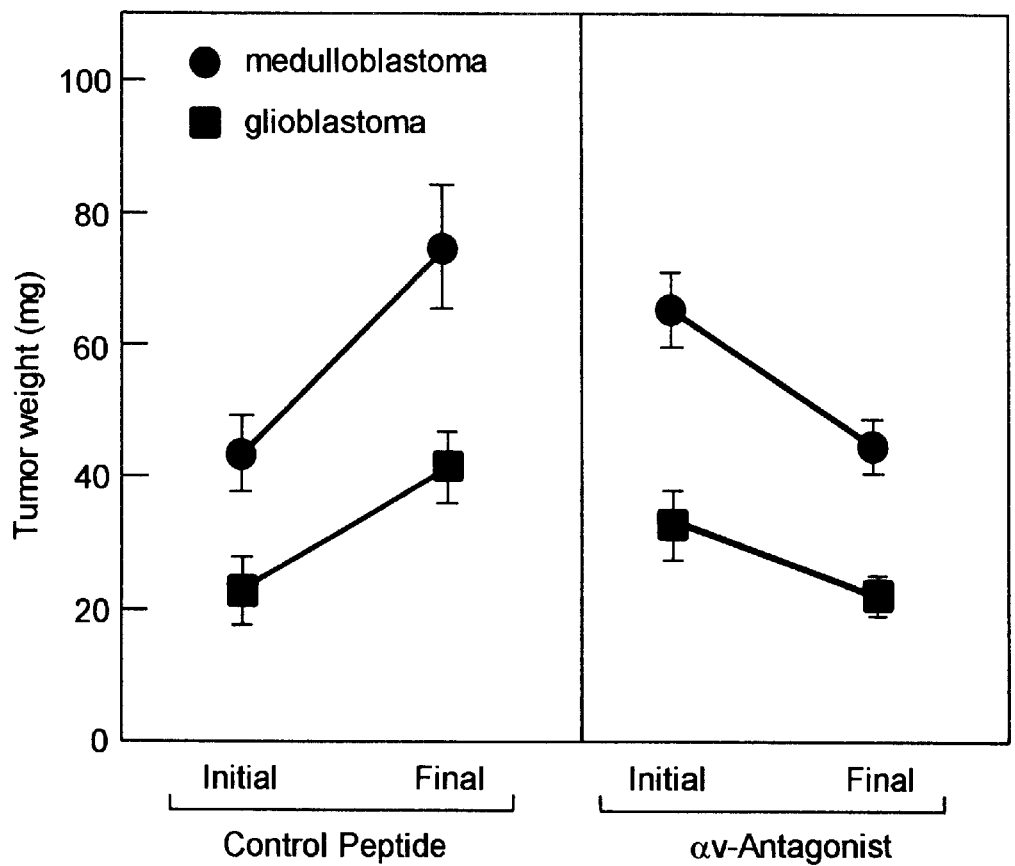

To assess the effect of αv antagonism on brain tumor associated angiogenesis, DAOY and U87MG human brain tumor cells were grown on chick chorioallantoic membranes (CAMs). The tumors were allowed to grow for 7 days before they were removed and reimplanted onto fresh CAMs. 24 hours after transfer, 100 μg of either the active cRGD peptide or control peptide (cRAD) was injected into a CAM vein. Tumors were grown for an additional 6 days and then weighed and analyzed for vascularization. Under stereomicroscope examination, tumors receiving the control peptide exhibited extensive angiogenesis, while tumors treated with the $α_v$-antagonist showed significant suppression of angiogenesis (FIG. 1a). Tumor growth was also inhibited by the ccv-antagonist. In contrast to control tumors, which increased 80% in weight, $α_v$-antagonist treated tumors decreased 30% in weight (FIG. 1b). These data suggest that the inhibition of tumor growth by αv-antagonism resulted as a consequence of disrupted tumor-associated angiogenesis.

FIGS. 1a and 1b show the inhibition of angiogenesis (a) and tumor growth on the CAM (b) by an $α_v$-antagonist. Brain tumors grown on CAMs were harvested and cut to similar sizes and placed on fresh CAMs of 10-day-old chicken eggs. The following day, 100 μg of active $α_v$-inhibitor or control peptide were injected into the chicken veins and grown for another 6 days. Eggs which received the control peptide showed significant angiogenesis (a) (DAOY=A and U87MG=C), while significant suppression of neovascularization was observed in the eggs receiving the active peptide (DAOY=B and U87MG=D). Tumors placed on the CAM were weighed at the beginning and end of the experiment (b). The weight of the tumors treated with the control peptide increased by 80% for both tumor types (left, n=8), whereas it decreased by about 30% when the active peptide was administered (right, n=8).

Orthotopic Tumor Model

Figure 2:
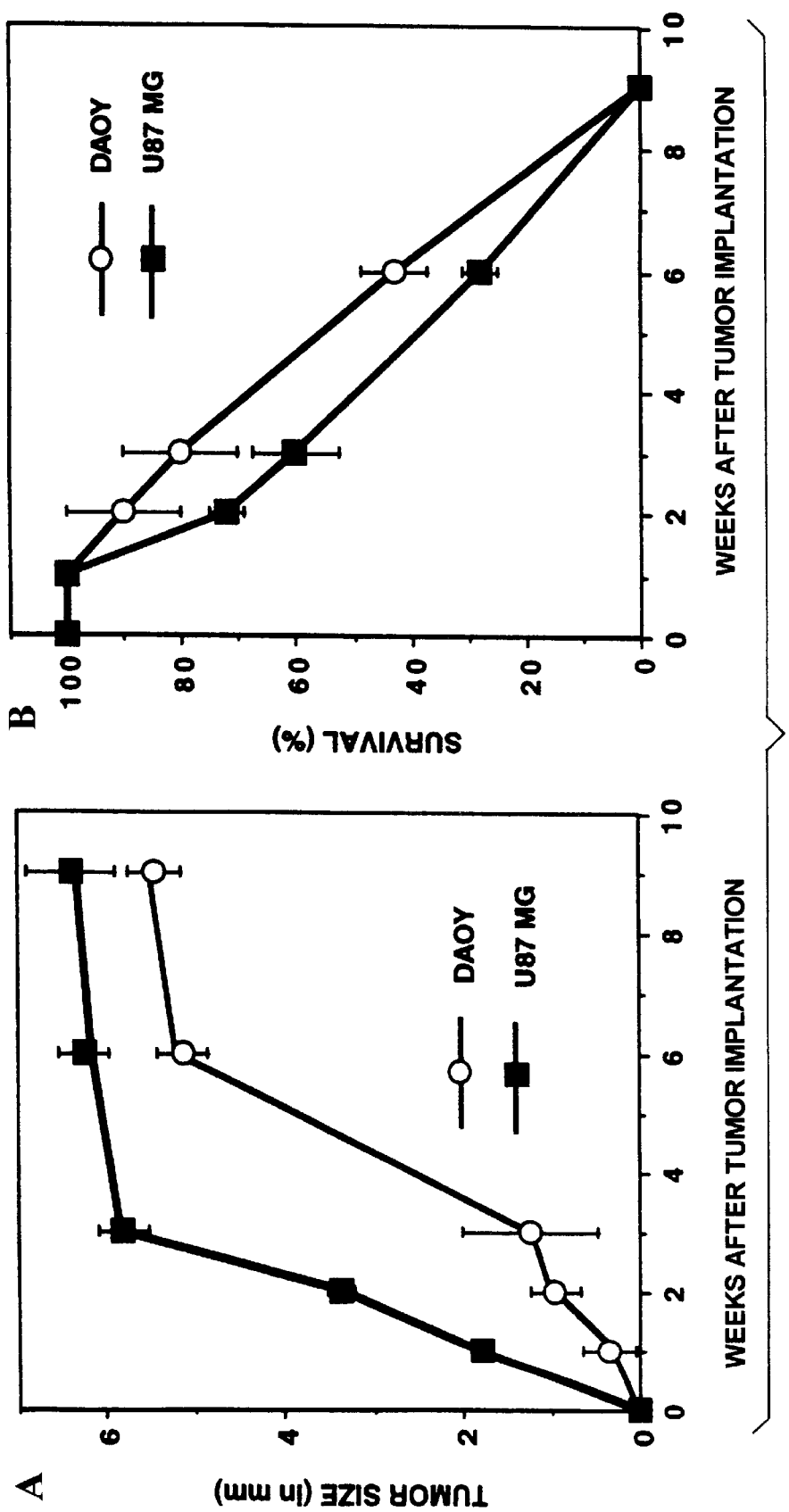
FIGS. 2(A and B) shows the tumor size (A) and mouse survival (B) after intracerebral injection of DAOY and U87MG cells.

DAOY and U87MG cells (10⁶ cells/mouse) were stereotactically injected into the right frontal cortex of nu/nu mice in order to establish a system that recapitulates the brain microenvironment. This method allowed for a highly reproducible model of human brain tumorigenesis and enabled the measurement of tumor growth and mouse survival over time prior to the introduction of αv-antagonism (FIGS. 2a and 2b). FIG. 2 shows the tumor size (A) and mouse survival (B) after intracerebral injection of DAOY and U87MG cells. U87MG cells show a rapid growth and reach a plateau of about 6 mm in 6 weeks, whereas the DAOY cells grow slower and reach a diameter of 5.5 mm in 9 weeks (A). All animals are dead by week 9 (B). For each time, point n=5 or 6.

Figure 3A:
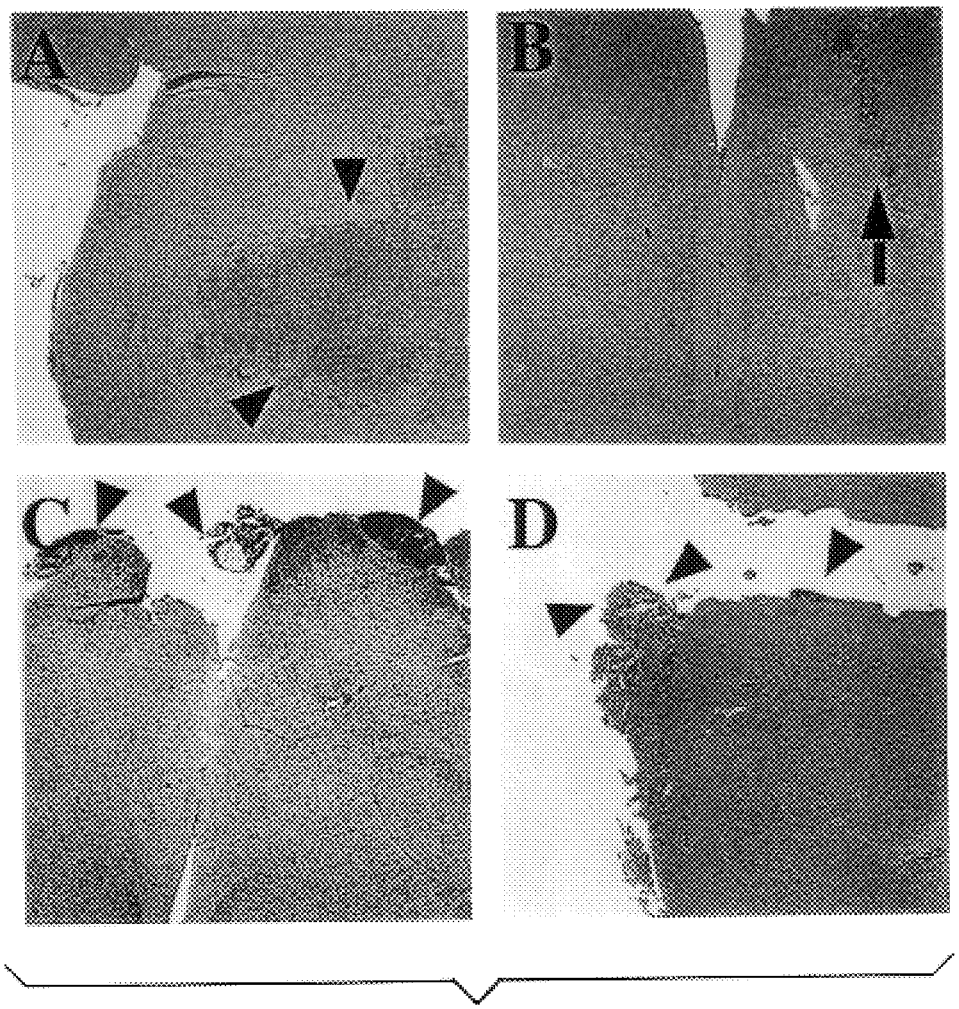
FIGS. 3a(A–D) and 3b(A–D) show histopathology of orthotopically injected brain tumor cells DAOY (a) and U87MG (b), daily treated with the inactive (A) or active peptide (B–D). Large intracerebral tumors (arrowheads) are visible in the control animals (A), whereas no tumors (B) or only microscopic residual tumors (arrowheads) are detected in the $\alpha_v$-antagonist-treated animals (C and D).
Figure 3B:
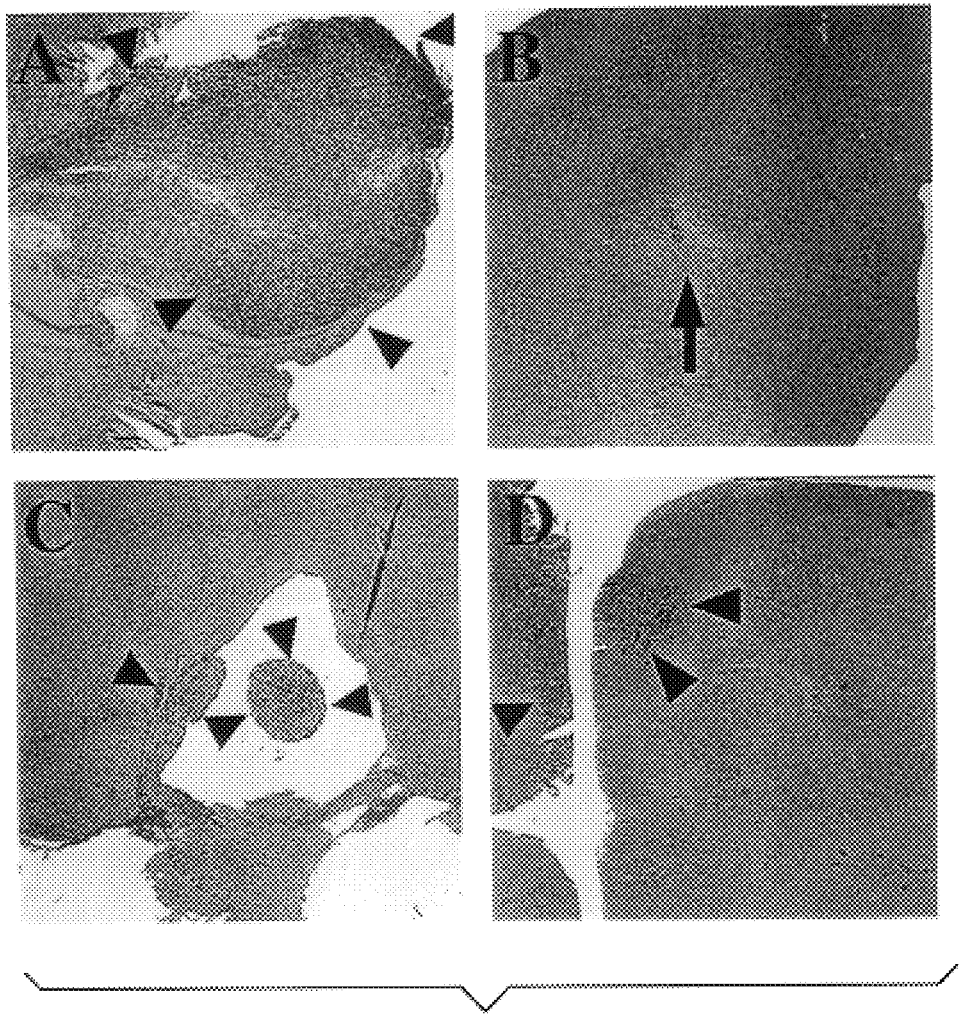

In order to test the effect of the cRGD peptide in this model, tumors were first grown for 7 days (DAOY) or 3 days (U87MG) before the daily i.p. administration of the $α_v$-antagonist (100 μg/mouse) or its inactive control for an additional 3 weeks. At the time of sacrifice (4 weeks total time of tumor growth), control mice had grossly visible brain tumors averaging 3mm (DAOY) and 5.5 mm (U87MG) in size. Treated mice had either no tumor or only scant residual tumor cells found in microscopic clumps along the ventricular and dural surfaces (FIGS. 3a and 3b). FIGS. 3a and 3b show the histopathology of orthotopically injected brain tumor cells DAOY (a) and U87MG (b), daily treated with the inactive (A) or active peptide (B-D). Large intracerebral tumors (arrowheads) are visible in the control animals (A), whereas no tumors (B) or only microscopic residual tumors (arrowheads) are detected in the $α_v$-antagonist-treated animals (C and D).

The treated mice also maintained their baseline weight of 21 g; however, the DAOY and U87MG control mice weighed 16 g and 15 g, respectively, representing a loss of 5–6 g from baseline weight (see Table 1). The mean time to the onset of neurologic symptoms in the control group was 2.5 weeks for U87MG and 4.5 weeks for DAOY mice, while treated animals showed no evidence of neurological symptoms at any time.

TABLE

| Cell Line | Tumor size (mm) | | Mouse weight (gr) |
| --- | --- | --- | --- |
| | Brain | Subcutis | |
| DAOY | | | |
| Control peptide | 3.0 ± 0.71 | 18 ± 1.41 | 16 ± 1.3 |
| Active peptide | NM | 17 ± 0.84 | 21 ± 0.89 |
| U87MG | | | |
| Control peptide | 5.5 ± 0.55 | 20 ± 1.0 | 15 ± 0.45 |
| Active peptide | NM | 19 ± 0.77 | 20 ± 0.71 |

NM = Not measurable

Figure 4:
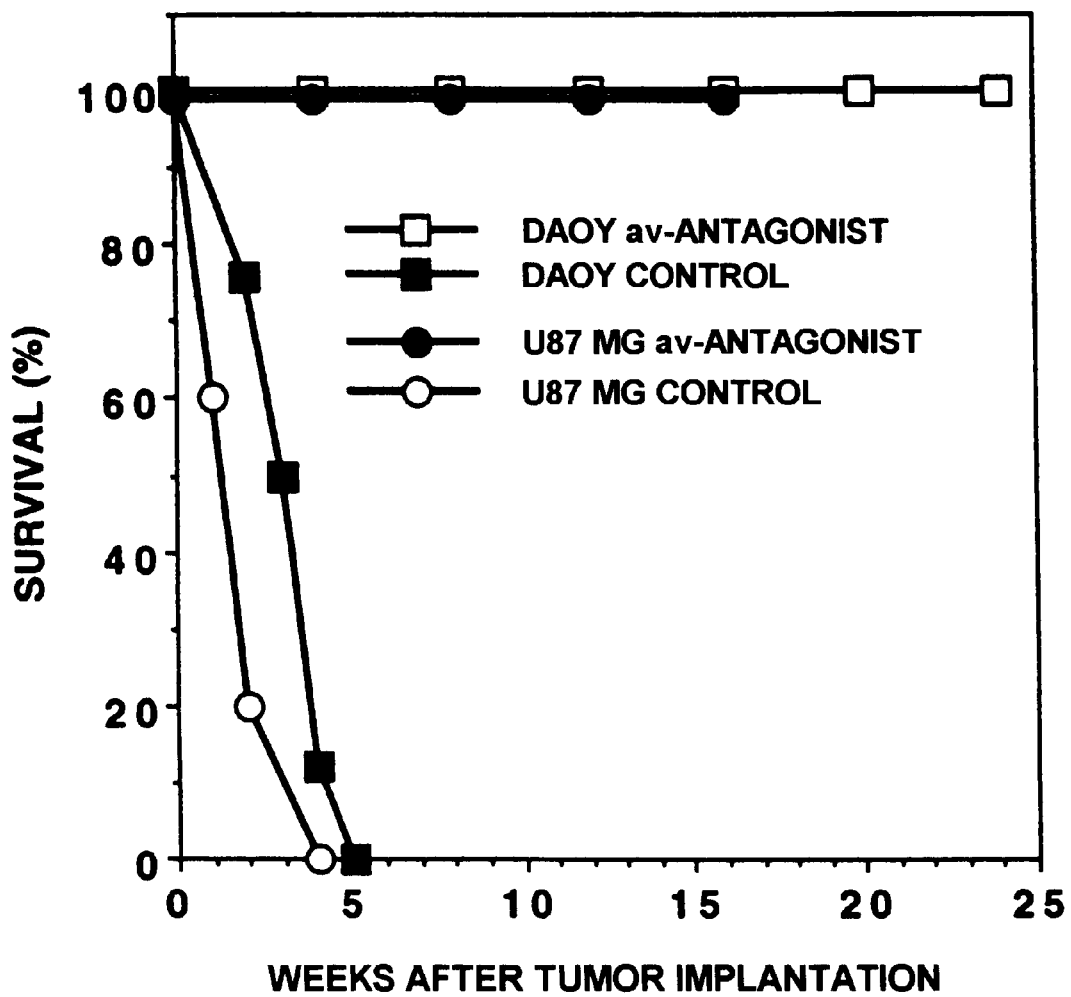
FIG. 4 shows the survival of mice after orthotopical brain tumor implantation, receiving either the active or inactive peptide.

Additional animals were tested for survival. Survival was measured as the time point in which mice required sacrifice, due to a moribund state. All control animals were sacrificed prior to 6 weeks tumor growth and the majority (>50%) in both control groups were sacrificed by weeks 3–4 (FIG. 4). FIG. 4 shows the survival of mice after orthotopical brain tumor implantation, receiving either the active or inactive peptide; i.p. treatment (100 μg/mouse/day) was initiated on day 3 for U87MG and day 7 for DAOY cells. N for DAOY and U87MG control is 16 mice each and 32 mice for treated DAOY and 24 for treated U87MG. FIG. 4 shows that none of the treated animals required sacrifice and, presently, the treated DAOY mice have survived up to 24 weeks and U87MG mice 15 weeks since tumor cell injection. None of the treated animals have developed any neurological signs and all continue to grow normally.

Heterotopic Tumor Model

To determine the influence of the microenvironment on tumor growth subjected to αv-antagonism, we injected the same human brain tumor cells subcutaneously ($10^6$ cells/nude mouse) before initiating treatment with the active and control peptides (100 μg/mouse daily i.p.) at 3 (U87MG) and 7 days after tumor cell injection (DAOY). Under these conditions, there was no inhibition of tumor growth by the active peptide, and after 6 weeks, the tumors from the treated and untreated groups appeared identical on both the macroscopic and microscopic level, each demonstrating the presence of extensive angiogenesis (data not shown). This indicates that the intrinsic properties of the brain tumor cells tested are not sufficient to render them sensitive to the activity of the cRGD peptide antagonist, but rather require conditions unique to the brain microenvironment.

Figure 5:
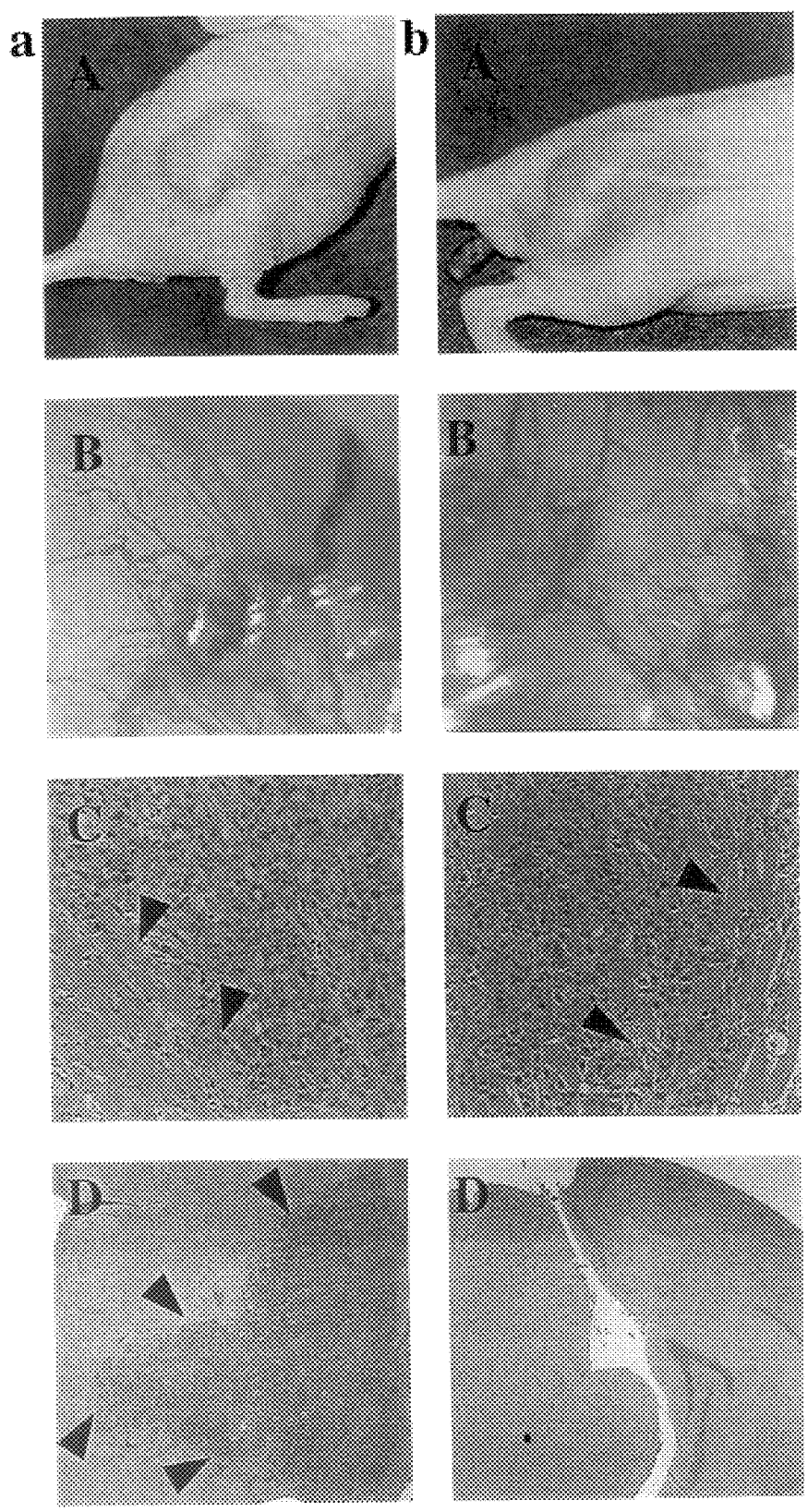
FIGS. 5(A, A–D) and (B, A–D) shows the effect of $\alpha_v$-antagonist on orthotopically (brain) and heterotopically (subcutis) implanted DAOY cells.

To further investigate this finding, we simultaneously injected the DAOY and U87MG cells intracranially and subcutaneously before initiating treatment with the peptides as outlined under the orthotopic model. FIG. 5 shows the effect of $\alpha_v$-antagonist on orthotopically (brain) and heterotopically (subcutis) implanted DAOY cells. Tumor cells ($10^6$) were injected into the brain and the subcutis and treatment with the inactive (a) or active peptide initiated on day 7 (b). Pictures were taken at week 4. Animals receiving either the inactive (a) or active (b) peptide showed a similar size of subcutaneous tumors (A) and vascularization (B). In both conditions, the s.c. tumors grew into the underlying muscle layer (arrowheads) (C). In contrast, the control animals developed large brain tumors (arrowheads), while the mice receiving the active peptide showed absence or microscopic residual disease (D). Therefore, FIG. 5 shows that the subcutaneous tumors in the control and treated groups both grew to an average size of 18 mm$^3$ with evidence of extensive vascularization (FIG. 5). The control mice also developed large brain tumors similar in size to that previously observed in the orthotopic tumor model, as well as clinical evidence of neurologic compromise (Table 1). In contrast, mice receiving the active peptide survived without evidence of neurologic symptoms, and necropsy revealed the absence of intracerebral tumor or only residual microscopic tumor cell clusters (FIG. 5). However, this group had progressive growth of their subcutaneous tumors, which necessitated sacrifice after 10 weeks. This confirmed that tumors growing intracerebrally are responsive to the treatment with the cyclic RGD peptide, while the same tumors growing subcutaneously are not.

Integrin Expression

Figure 6A:
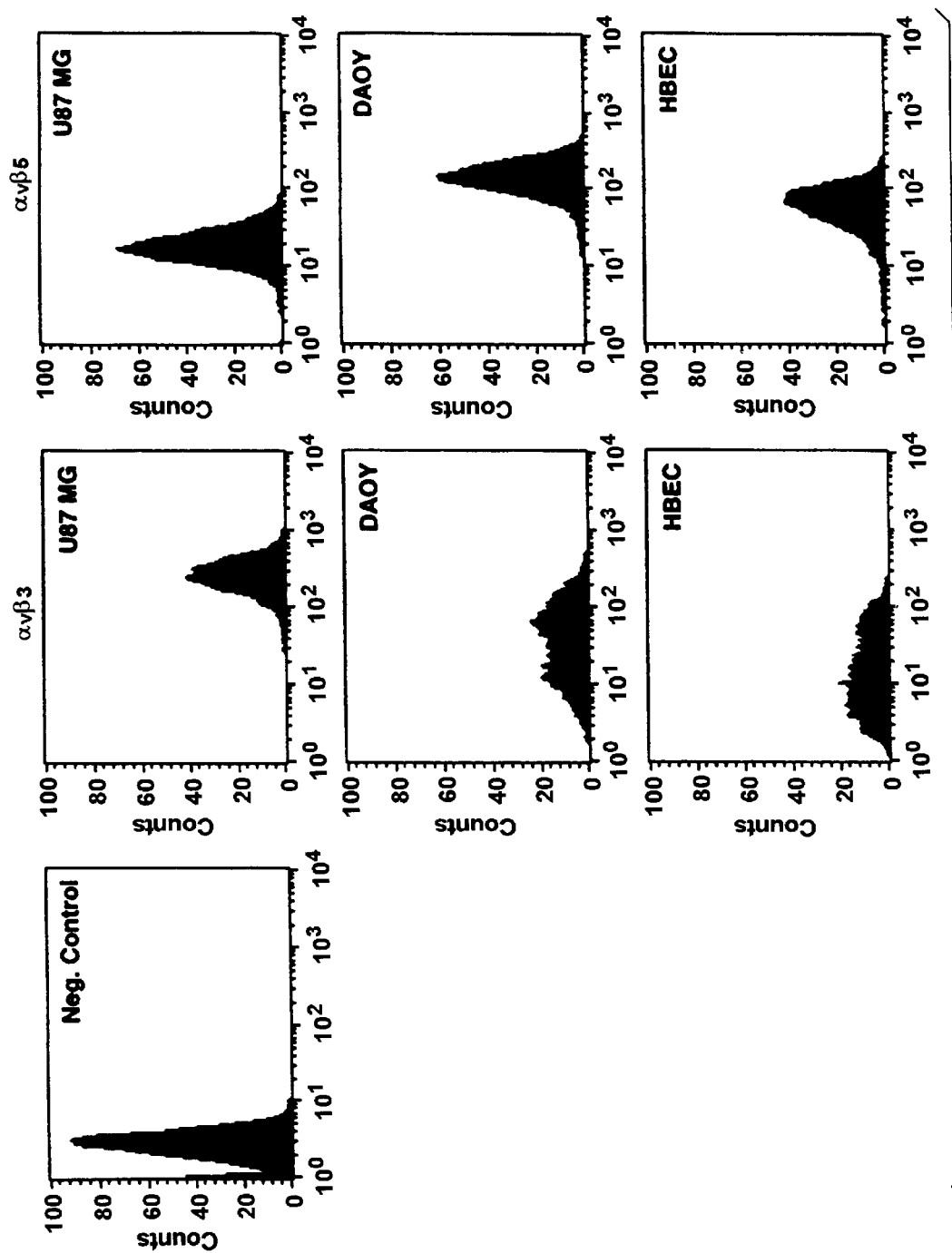
FIGS. 6a–6d show the integrin profile (a), and effect of $\alpha_v$-antagonist on adhesion to (b), migration on vitronectin (c) and cell viability on vitronectin (d) for brain tumor and brain capillary endothelial cells.

Vitronectin is a matrix protein which could influence the different biological responses observed in the brain and subcutaneous compartments. It is abundant in extraneural sites, but is not normally produced by glial and neuronal tissue (15, 20). However, malignant glioma cells synthesize vitronectin, which in turn may be crucial for allowing their attachment and spread (15). Alternatively, vitronectin may promote endothelial cell adhesion and migration toward the tumor bed and thus enhance angiogenesis. Since cell attachment to vitronectin is mediated by the integrins αvβ3 and αvβ5, we performed FACS analysis to determine whether the human DAOY medulloblastoma, U87MG glioblastoma and primary cultures of human brain endothelial cells (HBEC) express the integrins αvβ3 and αvβ5 (FIG. 6a).

FIGS. 6a–6d show the integrin profile (a), effect of $\alpha_v$-antagonist on adhesion to (b), migration on (c) and cell viability on vitronectin (d) for brain tumor and brain capillary endothelial cells. Both DAOY and U87MG tumor cells and brain capillary cells express the integrins $\alpha_v\beta_3$ and $\alpha_v\beta_5$ (a). Adhesion to vitronectin was significantly inhibited by the active peptide, as well as by the combination of antibodies to $\alpha_v\beta_3$ and $\alpha_v\beta_5$, while neither the control peptide nor the specific anti-$\alpha_v\beta_3$ nor anti-$\alpha_v\beta_5$ antibody alone had any significant effect. Migration of the cells on a vitronectin gradient was abolished by $\alpha_v\beta_3$ antibodies and the $\alpha_v$-antagonist, while neither the control peptide nor antibodies to $\alpha_v\beta_5$ had any inhibitory effect. Cell viability was tested by letting the cells attach to vitronectin for 1 hour, and then exposing them for 4 hours to the control peptide or $\alpha_v$-antagonist (20 μg/ml) (d). Adherent and floating cells were combined and examined by FACS for apoptosis, using FITC labeled anti-annexin V and propidium iodide. While little apoptosis was observed in the cultures exposed to the control peptide (d, left), both brain capillary endothelial cells and DAOY cells showed significant numbers of apoptotic cells (d, right).

FIGS. 6a–6d show that the U87MG cells express high levels of αvβ3 relative to DAOY cells, but the latter express higher amounts of αvβ5. HBEC cells grown in VEGF-containing medium express high amounts of αvβ5, while 50% of the cells express the αvβ3 integrin in short-term culture. Cells were also tested by FACS analysis, following 2 days growth in culture on plates coated with vitronectin. Expression of αvβ3 and αvβ5 did not change under these conditions (data not shown).

Vitronectin Adhesion

Figure 6B:
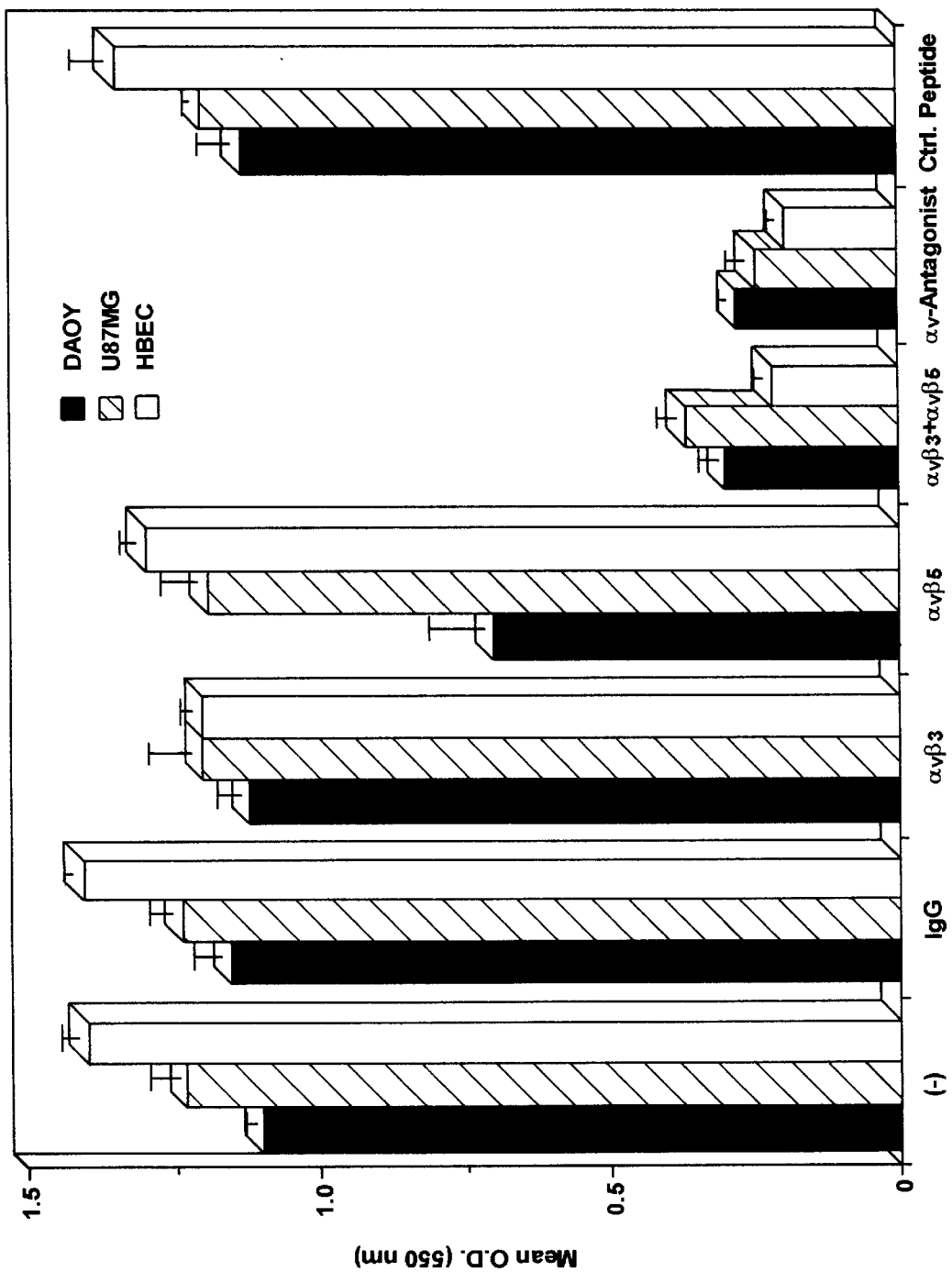

To determine if αvβ3 and αvβ5 regulate DAOY, U87MG and HBEC adhesion to vitronecin, the cells were plated in vitronectin-coated wells and allowed to adhere in the presence or absence of either blocking antibodies to αvβ3 (LM-609) and αvβ5 (P1-F6) or the cRGD peptide. P1-F6 minimally inhibited the attachment of DAOY cells, while LM-609 had no effect on the attachment of any of the cells. Significant inhibition of adhesion of all cells was observed by incubating P1-F6 and LM-609 together, or cRGD alone (FIG. 6b). These data indicate that blocking either integrin separately is insufficient and that dual blockade of αvβ3 and αvβ5 is required to significantly disrupt the vitronectin-dependent adhesion demonstrated by the cells tested.

Vitronectin Migration

Figure 6C:
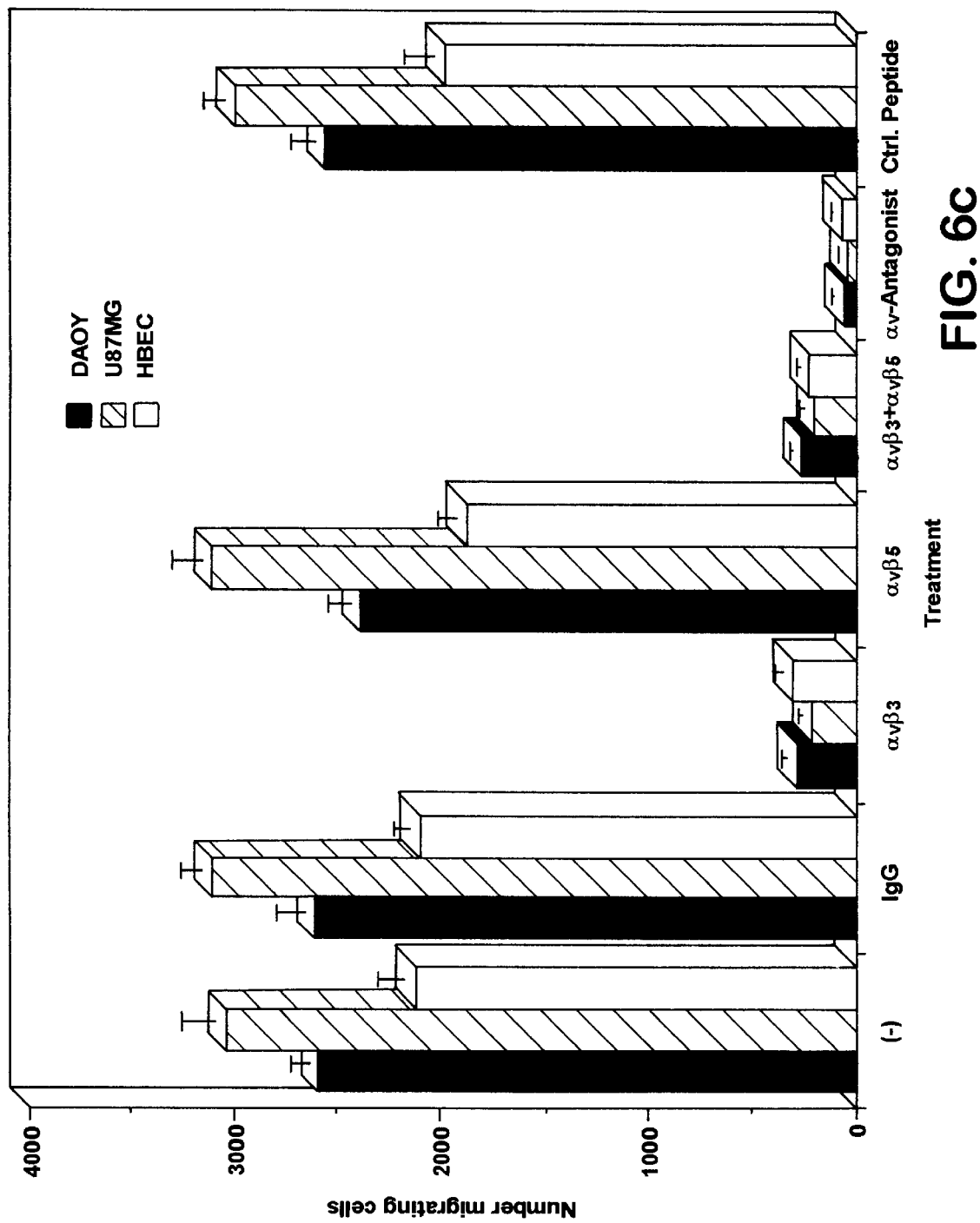

To address whether αvβ3 and αvβ5 modulate migration on vitronectin, independent of adhestion, we tested the same cells on vitronectin-coated membranes in Boyden chambers while in the presence of blocking antibodies or cRGD. P1-F6 did not effect migration; however, LM-609 and cRGD significantly inhibited the migration of all three cell types (FIG. 6c). Since LM-609, in the absence of P1-F6, was incapable of blocking adhesion, this anti-migratory effect must be mediated through a distinct pathway which is independent of forces responsible for adhesion. Furthermore, LM-609 blocked migration equally well as cRGD, suggesting that the αvβ3-mediated cell signaling is a critical component in the determination of the migration of the brain tumor and brain endothelial cells tested.

Apoptosis

Figure 6D:
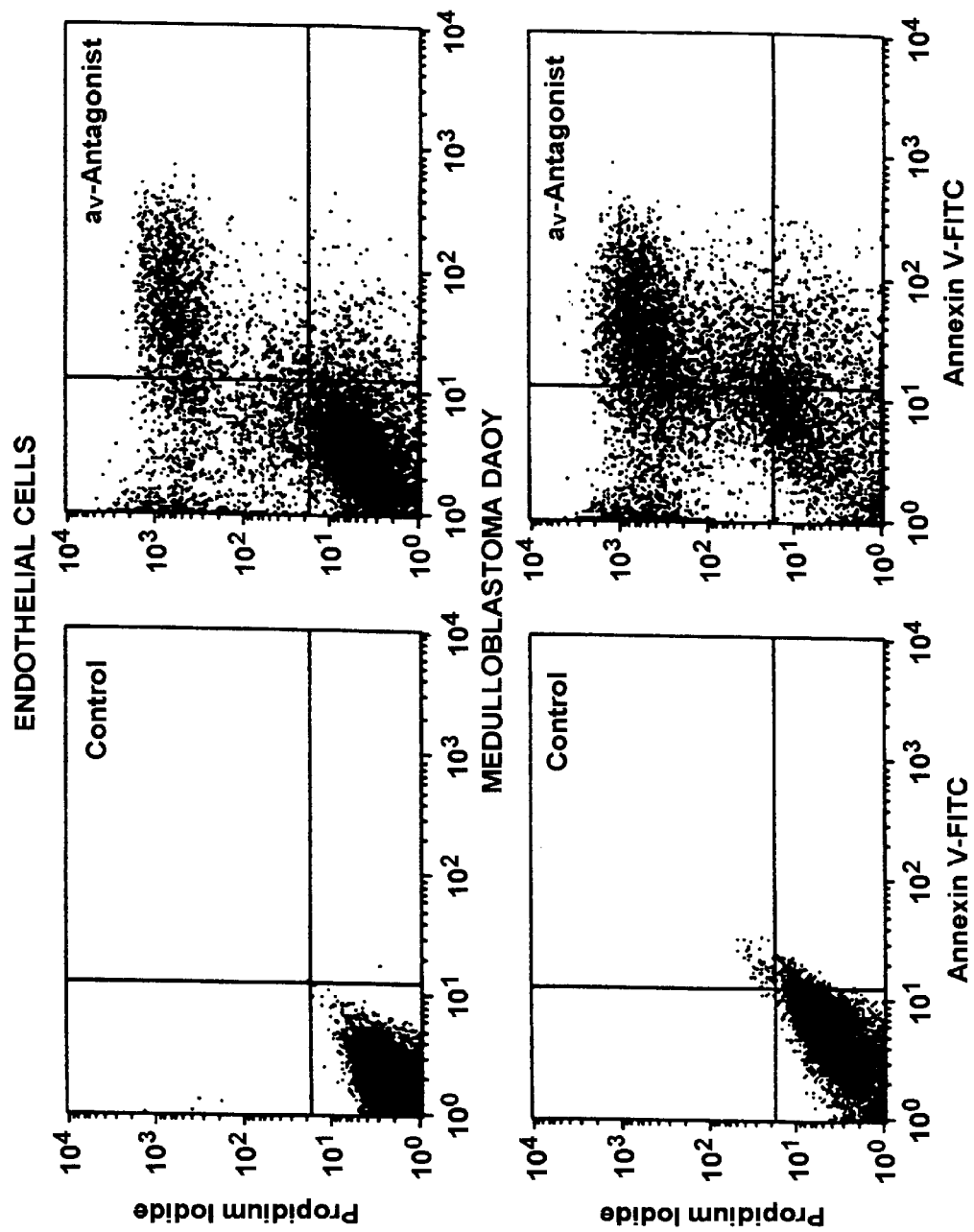

High-grade astrocytomas produce vitronectin at the leading invasive edge, suggesting that this protein plays an important role in brain tumor cell attachment, migration and possibly cell survival (15). We have previously shown that pre-incubation of brain tumor or capillary cells with the cRGD peptide, or the combination of anti-αvβ3 and anti-αvβ5 antibodies, prevents cell adhesion to vitronectin. Endothelial and melanoma cell apoptosis has been demonstrated, following similar inhibition of integrin-dependent attachment to matrix proteins (26–28). It was therefore of interest to determine whether the αv-antagonists could induce apoptosis of these cells after their detachment from vitronectin. DAOY cells and primary HBEC were seeded in adhesion buffer on vitronectin-covered wells (1 μg/ml) and allowed to attach for 30 min. at 37° C. The buffer was then replaced with buffer containing cRGD or cRAD peptide (control) at 20 μg/ml, and further incubated for 4 hrs. Attached cells were combined after trypsinization with floating cells and the number of apoptotic cells was determined by FACS, using anti-annexin V-FITC antibody and propidium iodide (Clontech Apo alert Annexin V-FITC detection apoptosis kit). Cells exposed to the control peptide cRAD showed little apoptosis, while both DAOY and HBEC cRGD-treated cells demonstrated significant apoptosis (FIG. 6d). These data indicate that cRGD peptide not only detaches these cells from vitronectin, but also induces their subsequent apoptosis.

Effect of Pentagentide on Brain Tumor Cell Adhesion to Different ECM Substrates

Figure 7:
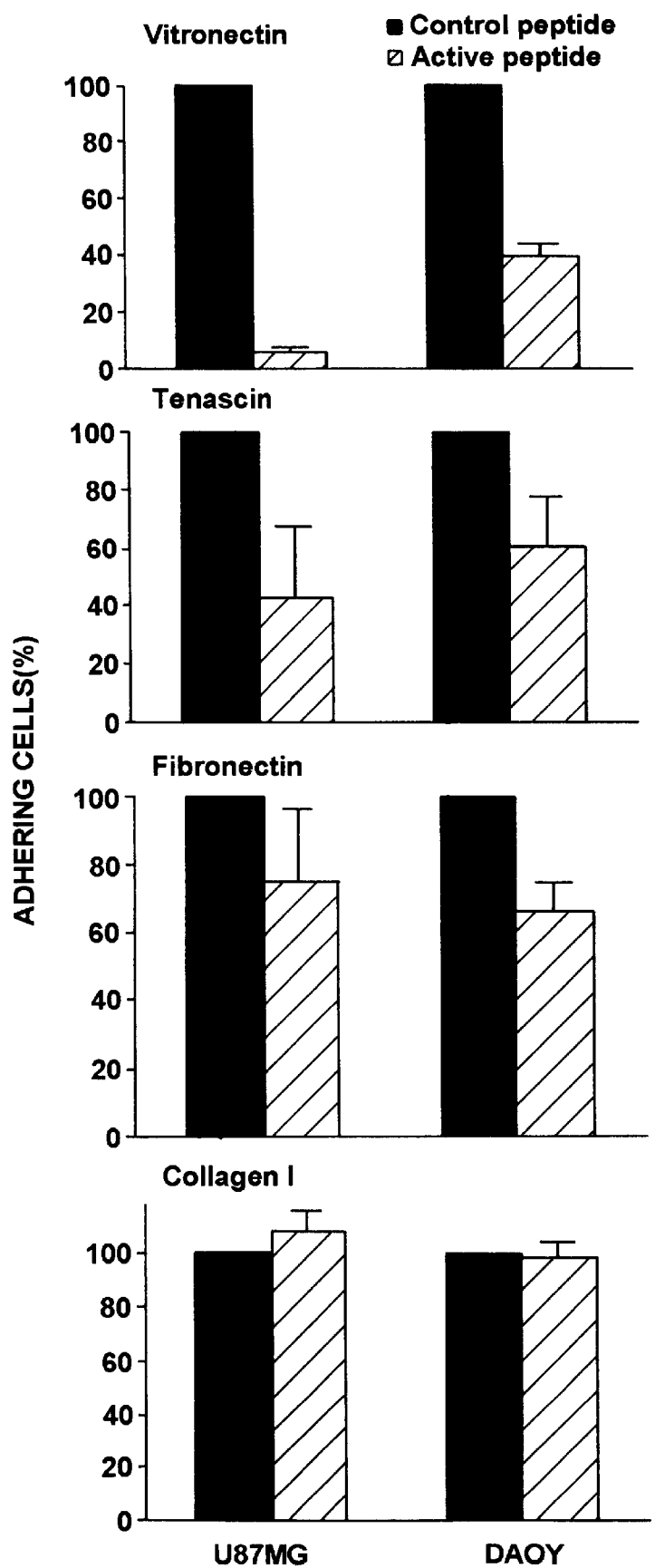
FIG. 7 shows the effect of cyclic pentapeptide on tumor cell adhesion to ECM proteins.

FIG. 7 shows the effect of cyclic pentapeptide on tumor cell adhesion to ECM proteins. Non tissue culture dishes were incubated 1 hour at 37° C. with vitronectin, tenascin, fibronectin or collagen I (10 μg/ml), then washed with PBS. After the wash, $5 \times 10^5$ cells /well were plated and incubated for 16 hours at 37° C. The cultures were then washed and an adhesion buffer containing 20 μg/ml of pentapeptide or control peptide were added and incubated for an additional 2–24 hours. The cultures were then washed twice with adhesion buffer and stained with Crystal violet and the OD 600 determined. The more adherent cells are present, the higher the OD. Data represent adherent cells after 8-hour incubation. U87=glioblastoma and DAOY=medulloblastoma.

As illustrated in FIG. 7, the tumor cells detached from vitronectin and tenascin, whose adherence is mediated by αv-integrins, but not from collagen and fibronectin, which interact with non αv-integrins. Similar data were obtained with brain capillary cells (not shown).

The Effect of Cell Detachment on Cell Survival

Figure 8:
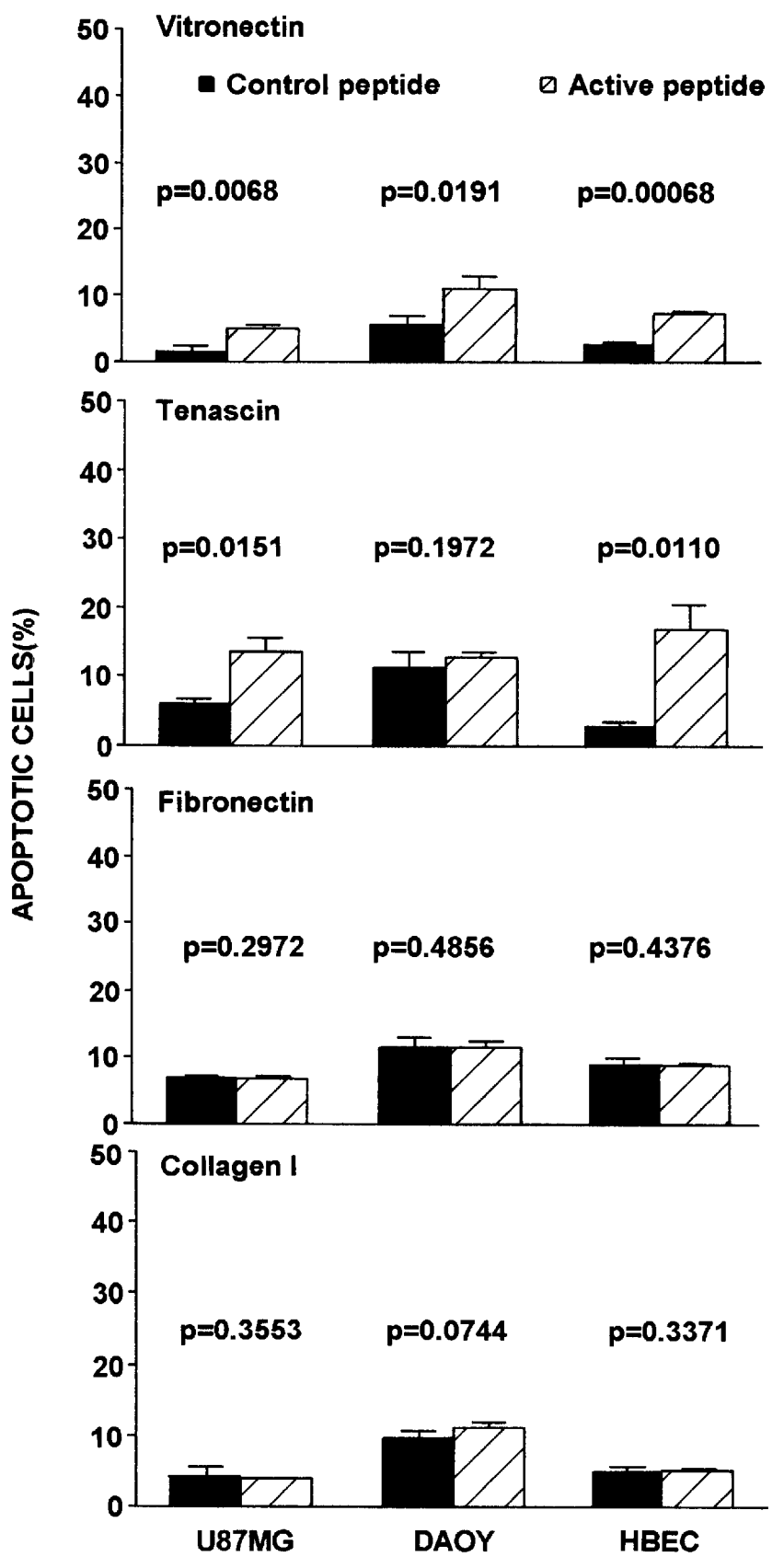
FIG. 8 shows the effect of inhibition of adhesion, resulting in cell death (apoptosis) in both brain tumor cells and brain capillary cells. This effect is restricted to the ECM vitronectin and tenascin.

FIG. 8 shows apoptosis of brain tumor and capillary cells grown on ECM and exposed to the pentapeptide. Test conditions were as in FIG. 7, except that detached cells and adherent cells were combined after trypsinisation. The cells were then washed, suspended in 50 μl PBS and centrifuged in glass cover slides (cytospin). After fixation with 4% paraformaldehyde, the cells were stained for apoptosis using the Boehringer Apoptosis Kit. Results are expressed in a percentage of apoptotic cells versus total number of cells. Experiment was done after 24 hours of incubation with the peptides.

The effect of cell detachment on cell survival is shown in FIG. 8. As shown, cells exposed to the active peptide for 24 hours and grown on vitronectin or tenascin showed increased number of dead cells when compared to control cells. In contrast, the pentapeptide did not alter the survival of cells grown on collagen I or fibronectin. Decreased cell survival was observed in both types of tumor cells and brain capillary cells. Similar data were obtained when the cells were stained for an early marker of cell death, expressed on the cell surface (Annexin-V, data not shown). Thus, the active pentapeptide induces cell detachment and death in both brain tumor and capillary cells adherent to vitronectin and tenascin.

Production of ECM Proteins in Human Brain Tumor

As outlined above, brain tumors produce vitronectin and tenascin in humans and it is thought that these substrates improve survival of tumor cells and enhance their invasion. We tested in our brain tumor model for the production of these proteins.

Figure 9:
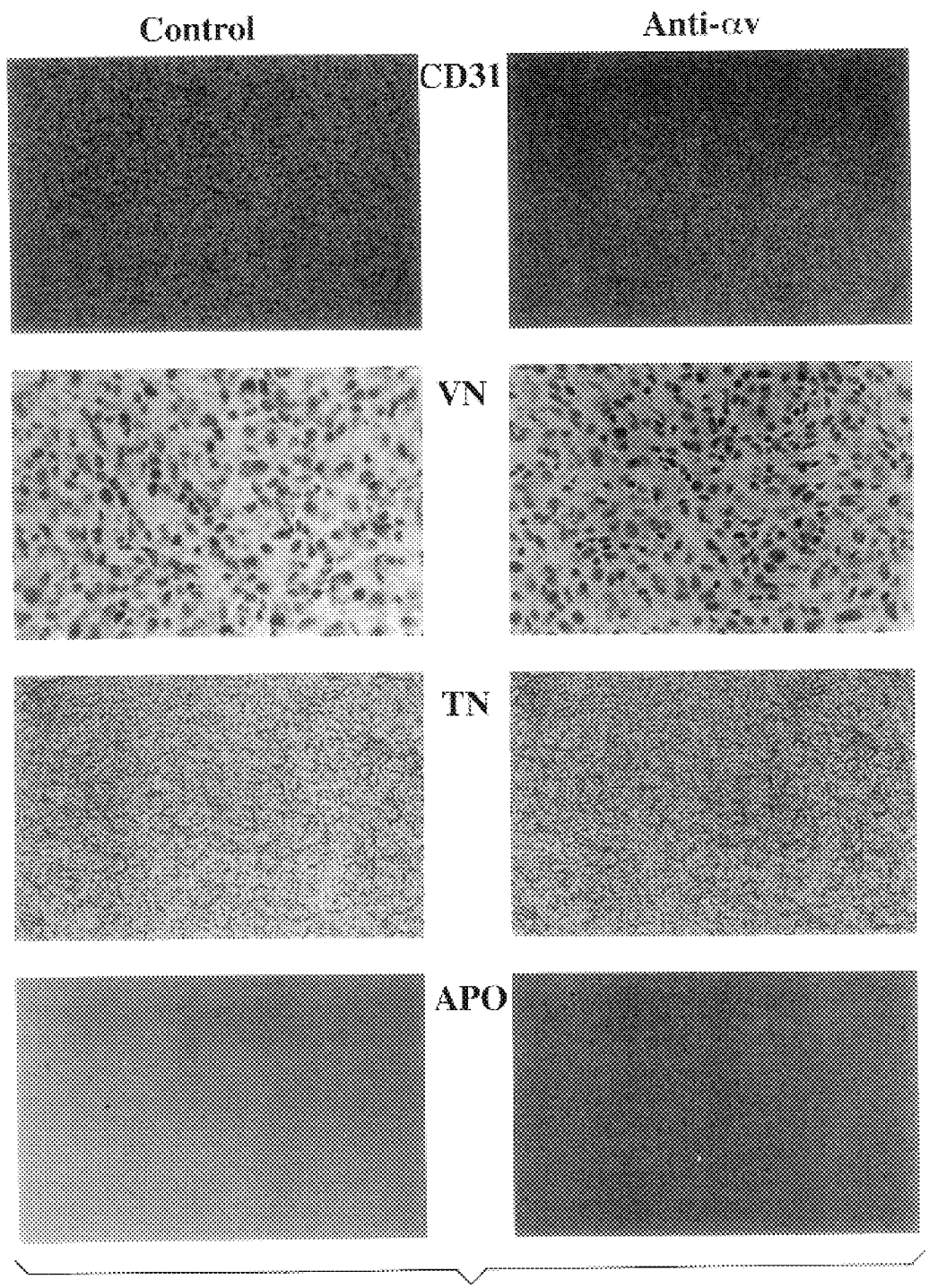
FIG. 9 shows the immunohistochemistry of U87 brain tumors xenotransplanted into the forebrain of nude mice and treated with an active (anti-αv) or control peptide.

FIG. 9 shows immunohistochemistry of U87 brain tumors xenotransplanted into the forebrain of nude mice and treated with active (anti-αv) or control peptide. Mice were injected with the tumor cells ($10^6$/cells/mouse) and treatment with the active or inactive peptide (100 μg/mouse/day) initiated on day 7 after injection. Tumors were removed after 2 weeks of treatment, fixed in buffered formalin, embedded in paraffin and 5 μm sections obtained. Sections were examined for CD31 expression (marker for capillary cells) using a monoclonal rat anti-mouse antibody (Pharmingen), monoclonal mouse anti-human vitronectin antibody (Sigma), mouse anti-human tenascin antibody (Neo-Marker) and the Boehringer Apoptosis Kit to test for dead cells. CD 31=capillary marker, VN=vitronectin, TN=tenascin and APO=apoptosis.

As shown in FIG. 9, the brain tumors indeed produced vitronectin and tenascin, and their origin from tumor cells was proven with the use of antibodies specific for human proteins. The administration of the active pentapeptide had no influence on the synthesis of these proteins. Furthermore, we were also able to demonstrate that the brain tumor cells produce these proteins in tissue culture (data not shown). Thus, our mouse model mimics the situation of human brain tumors.

The anti-angiogenic effect of the pentapeptide is shown at the top of FIG. 9, where we stained tissue sections for a specific marker for capillary cells, namely CD 31. While tumors treated with the control peptide had multiple vessels, which stained positive for this marker, there were very few such vessels in tumors treated with the active pentapeptide ($p<0.005$), indicating suppression of capillary growth. The bottom of FIG. 9 shows staining for apoptotic (dead) cells. The method is similar to that described in FIG. 8. Tumors treated with the active pentapeptide had significantly more dead cells than those treated with the control peptide ($p<0.02$). Pictures were taken for the glioblastoma U87, but similar data were obtained with the medulloblastoma DAOY (not shown).

Relationship of Cell Death with Tumor Cell Apoptosis

In order to demonstrate that this increased cell death is due to direct tumor cell apoptosis and not a consequence of the suppression of capillary growth, we implanted into mouse brains melanoma cells which either do (M21 L αv pos.) or do not (M21L αv neg.) express αv-integrinsα If mice transplanted with αv positive cells and treated with the active pentapeptide survive longer than mice treated with the control peptide, then direct tumor cell apoptosis must be responsible.

Table 2 shows the survival of mice with αvβ3 negative and positive tumors treated with RGDFV. Tumor cells ($10^6$) were injected into the forebrain of 6-week-old nude mice and treatment with the active or control peptide (100 μg/mouse/day) was initiated on day 3. Mice were sacrificed when becoming cachectic and the presence of tumor was verified by autopsy.

TABLE 2

| | Survival (days) | |
|---|---|---|
| Cell Line | EMD 121974 (active) | EMD 135981 (control) |
| M21Lαv neg | 15.7 ± 3.8 | 15.3 ± 3.3 |
| M21L4αv pos | 36.5 ± 2.9 | 17.3 ± 1.9 |

As shown in Table 2, mice transplanted with αv-negative melanoma cells survived 15 days, independent of treatment received. In contrast, the life span of mice with αv-positive tumors increased to 36 days when treated with the active pentapeptide, compared to 17 days when treated with the control peptide. This indicates that direct tumor cell apoptosis must be responsible for tumor cell death.

In conclusion, the above-discussed data support the hypothesis that the cyclic pentapeptide induces direct tumor cell death.

DISCUSSION

Brain tumors are highly angiogenic and are dependent on neovascularization for their continued growth. Anti-angiogenesis is thus a potentially important therapeutic strategy aimed against these malignancies. Integrins $\alpha v \beta 3$ and $\alpha v \beta 5$ are candidate anti-angiogenic targets, since their expression on endothelium is activated during angiogenesis (12,13). Their role in neovascularization was previously confirmed by studies which showed that angiogenesis induction by bFGF and TNF-alpha in the CAM could be disrupted by the presence of either the $\alpha v \beta 3$-blocking antibody LM-609 or an RGD cyclic peptide antagonist of $\alpha v \beta 3$ and $\alpha v \beta 5$ (21,23). In each case, the anti-angiogenesis effect is thought to occur through the induction of endothelial cell apoptosis as a result of preventing essential $\alpha v$-matrix protein binding interactions (28–30). In this study, we used a similarly specific RGD cyclic peptide antagonist of $\alpha v \beta 3$ and $\alpha v \beta 5$ (EMD 121974) and demonstrated its ability to inhibit CAM angiogenesis induced by two human brain tumor cell lines, DAOY and U87MG. cRGD treatment not only suppressed CAM angiogenesis, but subsequently led to tumor necrosis and tumor involution.

To address whether similar responses could be achieved in a model that recapitulates the brain microenvironment, brain tumor cells were stereotactically injected into the nude mouse forebrain. U87MG glioma and DAOY medulloblastoma cells were chosen to study because of their responsiveness to the peptide in the CAM assay and their extensive invasiveness and angiogenesis previously demonstrated in vivo (31,32). In this orthotopic model, cRGD again significantly inhibited U87MG and DAOY brain tumor growth. Control mice succumbed to tumor progression and were found to have highly invasive tumors larger than 3 mm$^3$ on average. The cRGD-treated mice survived without evidence of morbidity, and viable tumors could not be detected, apart from scant residual cells along the site of implantation or in small clusters along the ventricular and dural surfaces. All residual tumor foci in the treated group were smaller than 1 mm$^3$ and hence did not acquire a host angiogenesis response. Alternative inhibitors of angiogenesis, such as thrombospondin-1, TNP-470 and platelet factor 4, have also been shown to inhibit experimental brain tumor growth, although most of these results were limited to subcutaneous xenografts or required the direct delivery of drug to the tumor bed by stereotactic injection (32–34). A peptide antagonist of $\alpha v \beta 3$ in a SCID mouse/rat Leydig cell subcutaneous tumor model was shown to inhibit tumor growth by 80%, following its intraperitoneal administration (35). Angiostatin, an anti-angiogenic agent with an as yet unclear mechanism of action, also demonstrated considerable growth inhibition of intracranial C6 and 9L rat glioma xenografts (36). In contrast to our study, treatment with angiostatin (1 mg/mouse/day) or the peptidomimetic antagonist (2 mg/mouse/day) was initiated immediately after tumor cell implantation. Our study revealed near ablation of established tumor xenografts and is the first to show the inhibition of intracranial brain tumor growth and angiogenesis through integrin antagonism.

Interestingly, DAOY and U87MG tumors grown simultaneously under the skin showed little or no effect to cRGD treatment in our study. This underscores the importance of the extracellular environment in regulating host-tumor-cell integrin responses. Angiostatin was found to equally inhibit the growth of s.c. and i.c. injected brain tumor cells, indicating that this to compound suppresses angiogenesis through a different mechanism than the RGD peptide (36). One possible explanation for the difference in cRGD growth inhibition is that the endothelial cells of the subcutis may be inherently different from those of the CNS microvasculature, rendering angiogenesis less susceptible to integrin antagonism. This is supported by the recent finding that in $\alpha v$-knockout mice, only the brain and intestinal capillary cells are abnormal, while the remainder of the circulatory system is intact (37). Alternatively, matrix proteins, which serve as ligands for endothelial cell integrins, may be preferentially expressed by tumor cells, depending on an orthotopic or heterotopic location. For instance, human glioblastoma cells implanted subcutaneously were not found to produce vitronectin, however, their placement in the cerebral microenvironment induced their expression of the vitronectin gene (15). Normal brain tissue may likewise alter its expression of ECM proteins in response to invading glioma cells (38). Unlike extraneural sites, vitronectin is normally absent in the brain, and thus small changes in the concentration of this protein within the CNS may profoundly modify cell responses. Studies indicate that endothelial cell locomotion is dependent on the concentration of vitronectin and the distance between points of cell-matrix contacts which allow for cell spread (39,40).

The anti-tumorigenic effects of the peptide in our study are in general greater than those observed with other anti-angiogenic agents. Since many tumors also express $\alpha v \beta 3$ and $\alpha v \beta 5$ integrins (including U87MG and DAOY), the effect of integrin antagonists may not be limited to the host endothelium, although the importance of specific integrins in tumor cell responses is less clear (41). Prior studies have shown that the attachment of glioma, breast carcinoma, melanoma and HT29-D4 colonic adenocarcinoma cells to vitronectin is dependent on $\alpha v$ integrins (42–45). Vitronectin is produced by tumor and stromal cells and is most abundant at sites of tumor invasion and neovascularization, including malignant brain tumors (46,47). Thus vitronectin, in addition to supporting endothelial cell survival, may also be critical for enhancing the adhesion and invasion of tumor cells, which express $\alpha v \beta 3$ and $\alpha v \beta 5$. In a SCID mouse/human chimeric model for breast cancer, tumor invasion was markedly reduced following the administration of the anti-$\alpha v \beta 3$ antibody LM-609, suggesting a direct effect of $\alpha v \beta 3$ blockade upon the tumor is 5 independent of angiogenesis (48).

In order to address this question, we examined cellular adhesion and migration on vitronectin in the presence of $\alpha v$-antagonists, using DAOY, U87MG and isolated primary human brain endothelial cells (HBEC) (49). The anti-$\alpha v \beta 3$ antibody LM-609 inhibited U87MG, DAOY and HBEC migration on vitronectin, and in combination with the anti-$\alpha v \beta 5$ antibody P1-F6 inhibited the adhesion of these cells to vitronectin. cRGD alone significantly inhibited the adhesion to and migration on vitronectin by all three cell types. In a similar study, melanoma cell invasion was enhanced by vitronectin and blocked by RGD peptides (50). Finally, cRGD treatment resulted in increased apoptosis not only in HBEC cells, but also in DAOY and U87MG tumor cells as well. These results suggest that cRGD may act to inhibit tumor invasion and proliferation directly, in addition to its anti-angiogenic function.

Our data further demonstrates that cyclic pentapeptide may inhibit the adhesion of brain tumor cells to different ECM substrates such as vitronectin or tenascin. The effect of such an inhibition of adhesion resulted in cell death (apoptosis) in both brain tumor cells and brain capillary cells. This effect is restricted to the ECM vitronectin and tenascin. We have also demonstrated that the increased cell death is due to direct tumor cell apoptosis and not a consequence of the suppression of capillary growth. In other words, it is a discovery of the present invention that the cyclic pentapeptide induces direct tumor cell death.

In summary, this study provides evidence that targeted antagonism of integrins, specifically αvβ3 and αvβ5, can substantially inhibit brain tumorigenesis in vivo and may thus represent an important novel therapeutic approach to brain tumors. Our results also suggest that the microenvironment is critical to the tumor behavior and in determining its responsiveness to such biologically directed therapies. Finally, we show that integrin anatagonism can have an anti-tumorigenic effect independent of anti-angiogenesis, which may act synergistically to retard tumor growth.

The foregoing is meant to illustrate, but not to limit, the scope of the invention. Indeed, those of ordinary skill in the art can readily envision and produce further embodiments, based on the teachings herein, without undue experimentation.

REFERENCES

1. Folkman, J., The role of angiogenesis in tumor growth, *Sem. Cancer Biol.*, 3:65–71, 1992.
2. Plate, K. H., Risau, W., Angiogenesis in malignant gliomas, *Glia.*, 15:339–347, 1995.
3. Folkman, J., Watson, K., Ingber, D., Hanahan, D., Induction of angiogenesis during the transition from hyperplasia to neoplasia, *Nature*, 339:58–61, 1989.
4. Chan, A. S., Leunng, S. Y., Wong, M. P., Yuen, S. T., Cheung, N., Fan, Y. W., Chung, L. P., Expression of vascular endothelial growth factor and its receptors in the anaplastic progression of astrocytoma, oligodendroglioma, and ependymoma, *Am. J. Surg. Pathol.*, 22:816–826,1998.
5. Takano, S., Yoshii, Y., Kondo, S., Suzuki, H., Maruno, T., Shirai, S., Nose, T., Concentration of vascular endothelial growth factor in the serum and tumor tissue of brain tumor patients, *Cancer Res.*, 56:2185–2190, 1996.
6. Brem, S., Tsanaclis, A. M., Gately, S., Gross, J. L., Herblin, W. F., Immunolocalization of basic fibroblast growth factor to the microvasculature of human brain tumors, *Cancer*, 70:2673–2680, 1992.
7. Li, V. W., Folkerth, R. D., Watanabe, H., Yu, C., Rupnick, M., Barnes, P., Scott, R. M., Black, P. M., Sallan, S., Folkman, J., Microvessel count and cerebrospinal fluid basic fibroblast growth factor in children with brain tumors, *Lacet*, 344:82–86, 1994.
8. Abulrauf, S. I., Edvardsen, K., Ho K. L., Yang, X. Y., Rock, J. P., Rosenblum, M. L., Vascular endothelial growth factor expression and vascular density as prognostic markers of survival in patients with low-grade astrocytoma, *J. Neurosurg.*, 88:513–520, 1998.
9. Leon, S. P., Folkerth, R. D., Black, P. M., Microvessel density is a prognostic indicator for patients with astroglial brain tumors, *Cancer*, 77:362–372, 1996.
10. Hynes, R. O., Integrins: a family of cell surface receptor, *Cell*, 48:455–459, 1987.
11. Rusnati, M., Tanghetti, E., Dell'Era, P., Gualandris, A., Presta, M., Alphavbeta3 integrin mediates the cell-adhesive capacity and biological activity of basic fibroblast growth factor (FGF-2) in cultured endothelial cells, *Mol. Biol. Cell*, 8:2449–2461, 1997.
12. Varner, J. A., The role of vascular cell integrins alpha v beta 3 and alpha v beta 5 in angiogennesis, *EXS*, 79:361–390, 1997.
13. Friedlander, M., Brooks, P. C., Shaffer, R. W., Kincaid, C. M., Varner, J. A., Cheresh, D. A., Definition of two angiogenic pathways by distinct alphav integrins, *Science*, 270:1500–1502, 1995.
14. Gladson, G. L., Expression of integrin alpha v beta 3 in small blood vessels of glioblastoma tumors, *J. Neuropathol. Exp. Neurol.*, 55:1143–1149, 1996.
15. Gladson, C. L., Wilcox, J. N., Sanders, L., Gillespie, G. Y., Cheresh, D. A., Cerebral microenvironment influences expression of the vitronectin gene in astrocytic tumors, *J. Cell Sci.*, 108:947–956, 1995.
16. Longhurst, C. M., Jennings, L. K., Integrin-mediated signal transduction, *Cell Mol. Life Sci.*, 54:514–526, 1998.
17. Howe, A., Aplin, A. E., Alahari, S. K., Juliano, R. L., Integrin signaling and cell growth control, *Curr. Opin. Cell Biol.*, 10:220–231, 1998.
18. Malik, R. K., Regulation of apoptosis by integrin receptors, *J. Pediatr. Hematol. Oncol.*, 19:541–545, 1997.
19. Scatena, M., Almeida, M., Chisson, M. L., Fausto, N., Nicosia, R. F., Giachelli, C. M., NF-kappaB mediates alphavbeta3 integrin-induced endothelial cell survival, *J. Cell Biol.*, 141–1083–1093, 1998.
20 Gladson, C. L., Cheresh, D. A., Glioblastoma expression of vitronectin and the avb3 integrin. Adhesion mechanism for transformed glial cells, *J. Clin. Invest.*, 88:1924–1932, 1991.
21. Brooks, P. C., Clark, R. A., Cheresh, D. A., Requirement of vascular integrin alpha v beta 3 for angiogenesis, *Science*, 264:569–571, 1994.
22. Christofidou-Solomidou, M., Bridges, M., Murphy, G. F., Abelda, S. M., DeLisser, H M., Expression and function of endothelial cell av integrin receptors in wound-induced human angiogenesis in human skin/SCID mice chimeras, *Am. J. Pathol.*, 151:975–983, 1997.
23. Brooks, P. C., Montgomery, A. M., Rosenfeld, M., Reisfeld, R. A., Hu, T., Klier, G., Cheresh, D. A., Integrin avb3 antagonists promote tumor regression by inducing apoptosis of angiogenic blood vessels, *Cell*, 79:1157–1164, 1994.
24. Molema, G., Griffloen, A. W., Rocking the foundations of solid tumor growth by attacking the tumor's blood supply, *Immunol. Today*, 19:392–394, 1998.
25. Kim, K. J., Li, B., Winer, J., Armanini, M., Gillett, N., Phillips, H. S., Ferrara, N., Inhibition of vascular endothelial growth factor-induced angiogenesis suppresses tumor growth in vivo, *Nature*, 362–841–844, 1993.
26. Re, F., Zanetti, A., Sironi, M., Polentarutti, N., Lanfrancone, L., Dejana, E., Colotta, F., Inhibition of anchorage-dependent cell spreading triggers apoptosis in cultured human endothelial cells, *J. Cell Biol.*, 127:537–546, 1994.
27. Montgomery, A. M., Reisfffeld, R. A., Cheresh, D. A., Integrin avb3 rescues melanoma cells from apoptosis in three-dimensional dermal collagen, *Proc. Natl. Acad. Sci.*, 91:8856–8860, 1994.
28. Isik, F. F., Gibran, N. S., Jang, Y., Sandell, L., Schwartz, S. M., Vitronectin decreases microvascular 28. endothelial cell apoptosis, *J. Cell Physiol.*, 173:149–155, 1998.
29. Germer, M., Kanse, S. M., Kirkegaard, T., Kioler, L., Feldinng-Habermann, B., Goodman, S., Preissner, T., Kinetic analysis of integrin-dependent cell adhesion on vitronectin. The inhibitory potential of plasminogen activator inhibitor-1 and RGD peptides, *Eur. J. Biochem.*, 253:669–674, 1998.
30. Ruoslahti, E., Reed, J. C., Anchorage dependence, integrins, and apoptosis, *Cell*, 77:477–478, 1994.
31. MacDonald, T. J., Tabrizi, P., Shimada, H., Zlokovic, B. V., Laug, W. E., Detection of brain tumor invasion and micrometastasis in vivo by expression of enhanced green fluorescent protein, *Neurosurgery*, 43:1437–1443, 1998.
32. Hsu, S. C., Volpert, O. V., Steck, P. A., Mikkelsen, T., Polverini, P. J., Rao, S., Chou Bouck, N. P., Inhibition of angiogenesis in human glioblastomas by chromosome 10 induction of throbospondin-1, *Cancer Res.*, 56:5684–5691, 1996.
33. Taki, T., Ohnishi, T., Arita, N., Hiraga, S., Saitoh, Y., Izumoto, S., Mori, K., Hayakawa, T., Anti-proliferative effects of TNnP-470 on human malignant glioma in vivo: potent inhibition of tumor angiogenesis, *J. Neurooncol.*, 19:251–258, 1994.
34. Tanaka, T., Manome, Y., Wen, P., Kufe, D. W., Fine, H. A., Viral vector-mediated transduction of a modified platelet factor 4 cDNA inhibits angiogenesis and tumor growth, *Nat. Med.*, 3:437–442, 1997.
35. Carron, C. P., Meyer, D. M., Pegg, J. A., Engleman, V. W., Nickols, M. A., Settlel, S. L., Westlin, W. F., Ruminski, P. G., Nickols, G. A., A peptidomimetic antagonist of the integrin avb3 inhibits Leydig cell tumor growth and the development of hypercalcemia of malignancy, *Cancer Res.*, 58:1930–1935, 1998.
36. Kirsch, M., Strasser, J., Allende, R., Bello, L., Zhang, J., Black, P. M., Angiostatin suppresses malignant glioma growth in vivo, *Cancer Res.*, 58:4654–4659, 1998.
37. Bader, B. L., Rayburn, H., Crowley, D., Hynes, R. O., Extensive vasculogenesis, angiogenesis, and organogenesis precede lethality in mice lacking all αv integrins, *Cell*, 95:507–519, 1998.
38. Knott, J. C., Mahesparan, R., Garcia-Cabrera, I., Bolge, T. B., Edvardsen, K., Ness, G. O., Mark, S., Lund-Johansen, M., Bjerkvig, R., Stimulation of extracellular matric components in the normal brain by invading glioma cells, *Int. J. Cancer*, 75:864–872, 1998.
39. Seger, D., Gechtman, Z., Shaltiel, S., Phosphorylation of vitronectin by casein kinase II. Identification of the sites and their promotion of cell adhesion and spreading, *J. Biol. Chem.*, 273:24805–24813, 1998.
40. Woodard, A., Garcia-Cardera, G., Leong, M., Madri, J., Sessa, W., Languino, L., The synergistic activity of alphavb3 integrin and PDGF receptor increases cell migration, *J. Cell Sci.*, 111:469–478, 1998.
41. Sanders, R. J., Mainiero, F., Giancotti, F. G., The role of integrins in tumorigenesis and metastasis, *Cancer Invest.*, 16:329–344, 1998.
42. Treasurywala, S., Berens, M. E., Migration arrest in glioma cells is dependent on the alpha-v integrin subunit, *Glia*, 24:236–243, 1998.
43. Won, N. C., Mueller, B. M., Barbas, C. F., Ruminski, P., Quaranta, V., Lin, E. C., Smith, J. W., Alpha-v integrins mediate adhesion and migration of breast carcinoma cell lines, *Clin. Exp. Metastasis*, 16:50–61, 1998.
44. Van Leeuwen, R. L., Yoshinaga, I. G., Akasaka, T., Dekker, S. K., Vermeer, B. J., Byers, H, R., Attachment, spreading and migration of melanoma cells on vitronectin. The role of alpha v beta 3 and alpha v beta 5 integrins, *Exp. Dermatol.*, 5:308–315, 1996.
45. Lehmann, M., El Battari, A., Abadie, B., Martin, J. M., Marvallidi, J., Role of alpha v beta 5 and alpha v beta 6 integrin glycosylation in the adhesion of a colonic adenocarcinoma cell line (HT29-D4), *J. Cell Biochem.*, 61:266–277, 1996.
46. Kost, C., Benner, K., Stockmann, A., Linder, D., Preissner, K. T., Limited plasmin proteolysis of vitronectin. Characterization of the adhesion protein as morpho-regulatory and angiostatin binding factor, *Eur. J. Biochem.*, 236:682–688, 1996.
47. Maenpaa, A., Kovanen, P. E., Paetau, A., Jaaskelainen, J., Timonen, T., Lymphocyte adhesion molecule ligands and extracellular matrix proteins in gliomas and normal brain: expression of VCAM-1 in gliomas, *Acta. Neuropathol.*, 94:216–225, 1997.
48. Brooks, P. C., Stromblad, S., Klemke, R., Visscher, D., Sarkar, F. H., Cheresh, D. A., Anti-integrin alpha v beta 3 blocks human breast cancer growth and angiogenesis in human skin, *J. Clin. Invest.*, 96:1815–1822, 1995.
49. Stins, M. F., Gillesl, F., Kim, K. S., Selective expression of adhesion molecules on human brain microvascular endothelial cells, *J. Neuroimmunol.*, 76:81–90, 1997.
50. Bafetti, L. M., Young, T. N., Itoh, Y., Stack, M. S., Intact vitronectin induces matrix metalloproteinase-2 and tissue inhibitor of metalloproteinase-2 expression and enhanced cellular invasion by melanoma cells, *J. Biol. Chem.*, 273:143–149, 1998.
51. Wong, N. C., Mueller, B. M., Barbas, C. F., Ruminski, P., Quaranta, V., Lin, E. C., Smith, J. W., Alphav integrins mediate adhesion and migration of breast carcinoma cell lines, *Clin. Exp. Metastasis*, 16:50–61, 1998.
52. Van Leeuwen, R. L., Yoshinaga, I. G., Akasaka, T., Dekker, S. K., Vermeer, B. J., Byers, H. R., Attachment, spreading and migration of melanoma cells on vitronectin. The role of alpha v beta 3 and alpha v beta 5 integrins, *Exp. Dermatol.*, 5:308–315, 1996.
53. Lehmann, M., El Battari, A., Abadie, B., Martin, J. M., Marvaldi, J., Role of alpha v beta 5 and alpha v beta 6 integrin glycosylation in the adhesion of a colonic adenocarcinoma cell line (HT29-D4), *J. Cell Biochem.*, 61:266–277, 1996.
54. Gladson, C. L., Cheresh, D. A., Glioblastoma expression of vitronectin and the integrin, *J. Clin. Invest.*, 88:1924–1932, 1991.
55. Jaskiewicz, K., Chasen, M. R., Robson, S. C., Differential expression of extracellular matrix proteins and integrins in hepatocellular carcinoma and chronic liver disease, *Anticancer Res.*, 13:2229–2237, 1993.
56. Brooks, P. C., Stromblad, S., Klemke, R., Visseher, D., Sarkar, F. H., Cheresh, D. A., Anti-integrin alpha v beta 3 blocks human breast cancer growth and angiogenesis in human skin, *J. Clin. Invest.*, 96:1815–1822, 1995.
57. Leon, S. P., Folkerth, R. D., Black, P. M., Microvessel density is a prognostic indicator for patients with astroglial brain tumors, *Cancer*, 77:362–372, 1996.

58. Wesseling, P., Van Der Laak, J. A., Link, M., Teepen, H. L., Ruiter, D. J., Quantitative analysis of microvascular changes in diffuse astrocytic neoplasms with increasing grade of malignancy, *Hum. Pathol.*, 29:352–358, 1998.
59. Li, V. W., Folkerth, R. D., Watanabe, H., Yu, C., Rupnick, M., Bames, P., Scott, M., Black, P. M., Sallan, S., Folkman, J., Microvessel count and cerebrospinal fluid basic fibroblast growth factor in children with brain tumors, *Lancet*, 344:82–86, 1994.
60 Taki, T., Ohnishi, T., Arita, N., Hiraga, S., Saitoh, Y., Izumoto, S., Mori, K., Hayakawa, T., Anti-proliferative effects of TNP-470 on human malignant glioma in vivo: potent inhibition of tumor angiogenesis, *J. Neurooncol.*, 19:251–258, 1994.
61. Hsu, S. C., Volpert, O. V., Steck, P. A., Mikkelsen, T., Polverini, P. J., Rao, S., Chou Bouck, N. P., Inhibition of angiogenesis in human glioblastomas by chromosome 10 induction of thrombospondin-1, *Cancer Res.*, 56:5684–5691, 1996.
62. Tanaka, T., Manome, Y., Wen, P., Kufe, D. W., Fine, H. A., Viral vector-mediated transduction of a modified platelet factor 4 CDNA inhibits angiogenesis and tumor growth, *Nat. Med.*, 3:437–442, 1997.

What is claimed is:

1. A method of inhibiting intracerebral tumor growth in the brain of a host, comprising administering to the host in need of such an inhibition a therapeutically effective amount of an antagonist of $\alpha_v$ integrin which is cyclo (Arg-Gly-Asp-D-Phe-[N-Me]-Val).

2. A method for inhibiting extracellular matrix (ECM)-dependent cell adhesion in intracerebral brain tumor cells growing in the brain of a host, comprising administering to the host a therapeutically effective amount of an antagonist of $\alpha_v$ integrin which is cyclo (Arg-Gly-Asp-D-Phe-[N-Me]-Val).

3. A method for inhibiting vitronectin-dependent cell migration in intracerebral brain tumor cells growing in the brain of a host, comprising administering to the host a therapeutically effective amount of an antagonist to $\alpha_v\beta_3$ which is cyclo(Arg-Gly-Asp-D-Phe-[N-Me]-Val).

4. A method of inducing apoptosis in intracerebral tumor cells growing in the brain of a host, comprising administering to the host a therapeutically effective amount of an antagonist of $\alpha_v$ integrin which is cyclo(Arg-Gly-Asp-D-Phe-[N-Me]-Val).

* * * * *